United States Patent
Lauring et al.

(10) Patent No.: US 12,036,203 B2
(45) Date of Patent: Jul. 16, 2024

(54) METHODS OF TREATING OR REDUCING THE RISK OF CARDIOVASCULAR EVENTS AND RELATED DISEASES USING SGLT-2 INHIBITORS

(71) Applicants: Merck Sharp & Dohme LLC, Rahway, NJ (US); Pfizer Inc., New York, NY (US)

(72) Inventors: Brett Lauring, Tenafly, NJ (US); Samuel S. Engel, New York, NY (US); Steven G. Terra, Middleton, MA (US); James M. Rusnak, Hollis, NH (US)

(73) Assignees: Merck Sharp & Dohme LLC, Rahway, NJ (US); Pfizer Inc., New York, NY (US)

( * ) Notice: Subject to any disclaimer, the term of this patent is extended or adjusted under 35 U.S.C. 154(b) by 1 day.

(21) Appl. No.: 16/597,894

(22) Filed: Oct. 10, 2019

(65) Prior Publication Data

US 2020/0038368 A1 Feb. 6, 2020

Related U.S. Application Data

(63) Continuation of application No. 16/079,596, filed as application No. PCT/US2017/020849 on Mar. 6, 2017, now abandoned.

(60) Provisional application No. 62/306,907, filed on Mar. 11, 2016.

(51) Int. Cl.
| | | |
|---|---|---|
| *A61K 31/357* | (2006.01) | |
| *A61K 31/155* | (2006.01) | |
| *A61K 31/4985* | (2006.01) | |
| *A61K 31/7048* | (2006.01) | |
| *A61P 9/04* | (2006.01) | |
| *A61P 9/10* | (2006.01) | |

(52) U.S. Cl.
CPC .......... *A61K 31/357* (2013.01); *A61K 31/155* (2013.01); *A61K 31/4985* (2013.01); *A61K 31/7048* (2013.01); *A61P 9/04* (2018.01); *A61P 9/10* (2018.01)

(58) Field of Classification Search
CPC .................................................. A61K 31/357
See application file for complete search history.

(56) References Cited

U.S. PATENT DOCUMENTS

| | | | | |
|---|---|---|---|---|
| 8,080,580 B2 * | 12/2011 | Mascitti | .................. | A61P 27/00 514/456 |
| 2010/0056618 A1 | 3/2010 | Mascitti et al. | | |
| 2013/0137646 A1 | 5/2013 | Wienrich et al. | | |
| 2014/0303097 A1 * | 10/2014 | Broedl | .................. | A61K 9/2866 514/23 |

FOREIGN PATENT DOCUMENTS

WO 2016077126 A1 5/2016

OTHER PUBLICATIONS

Cardiovascular Outcomes Following Treatment With Ertugliflozin in Participants With Type 2 Diabetes Mellitus and Established Vascular Disease (MK-8835-004), ClinicalTrials.gov, 2013, p. 1-4.
Inzucchi, S.E. et al., SGLT-2 inhibitors and cardiovascular risk: Proposed pathways and review of ongoing outcoume trials, Diabetes & Vascular Disease Research, 2015, p. 90-100, vol. 12, No. 2.
Liu, J. et al., Why Do SGLT2 Inhibitors Inhibit Only 30-50% of Renal Glucose Reabsorption in Humans?, Diabetes, 2012, p. 2199-2204, vol. 61.
Zinman, B. et al., Empagliflozin, Cardiovascular Outcomes, and Mortality in Type 2 Diabetes, The New England Journal of Medicine, 2015, p. 2117-2128, vol. 373.
U.S. Appl. No. 16/079,596, filed Aug. 24, 2018.
German Ramirez et al., Clinical Practice Considerations and review of the Literature for the use of DPP-4 Inhibitors in Patients with Type 2 Diabetes and Chronic Kidney Disease, Endocrine Practice, 2013, pp. 1025-1034, 19.
Kumbhani, Dharam, Evaluation of Ertugliflozin Efficacy and Safety Cardiovascular Outcomes Trial—Vertis CV, American College of Cardiology, 2020, 1-5, N/A.
Low Wang, Cecilia C. et al., Cardiovascular Safety Trials for All New Diabetes Mellitus Drugs?, Circulation, 2019, 1741-1743, 139.
Udell, Jacob A. et al., Glucose-lowering drugs or strategies and cardiovascular outcomes in patients with or at risk for type 2 diabetes: a meta-analysis of randomised controlled trials, Lancet Diabetes Endocrinol, 2015, 356-366, 3.
Das, Uday Sankar et al., SGLT2 inhibitors in heart failure with reduced ejection fraction, The Egyptian Heart Journal, 2021, 1-7, 73:93.
Fediuk, Daryl J. et al., End-to-end application of model-informed drug development for ertugliflozin, a novel sodium-glucose cotransporter 2 inhibitor, CPT Pharmacometrics Syst. Pharmacol., 2021, 529-542, 10.
C. P. Cannon, et al., Cardiovascular Outcomes with Ertugliflozin in Type 2 Diabetes, The New England Journal of Medicine, Oct. 8, 2020, 1425-35, 383.

\* cited by examiner

*Primary Examiner* — Marcos L Sznaidman
(74) *Attorney, Agent, or Firm* — Janet E. Fair; Alysia A. Finnegan

(57) ABSTRACT

The present invention relates to the use of certain SGLT-2 inhibitors, such as ertugliflozin or a pharmaceutically acceptable salt or a co-crystal thereof, for treating, reducing the risk of and/or preventing heart failure, myocardial infarction, cardiovascular disease or cardiovascular death in animals without type 2 or type 1 diabetes mellitus, or in animals with pre-diabetes, or in animals with type 2 or type 1 diabetes mellitus or pre-diabetes.

4 Claims, No Drawings

METHODS OF TREATING OR REDUCING THE RISK OF CARDIOVASCULAR EVENTS AND RELATED DISEASES USING SGLT-2 INHIBITORS

CROSS-REFERENCE TO RELATED APPLICATIONS

This application is a continuation of U.S. patent Ser. No. 16/079,596 which is a U.S. National Phase application under 35 U.S.C. § 371 of PCT Application No. PCT/US2017/020849, filed Mar. 6, 2017, which published as WO2017/155481 A1 on Sep. 14, 2017, and claims priority under 35 U.S.C. § 365(b) from U.S. provisional patent application No. 62/306,907, filed Mar. 11, 2016.

FIELD OF THE INVENTION

The present invention relates to the use of certain SGLT-2 inhibitors, such as ertugliflozin or a pharmaceutically acceptable salt or a co-crystal thereof, for treating, reducing the risk of and/or preventing heart failure, myocardial infarction, cardiovascular disease or cardiovascular death in animals, preferably humans, without type 2 or type 1 diabetes mellitus or pre-diabetes, or in animals, preferably humans, with type 2 or type 1 diabetes mellitus or pre-diabetes.

BACKGROUND

Sodium-glucose co-transport (SGLT) inhibitors have been found to be effective in treating pre-diabetes, type 1 or type 2 diabetes mellitus. Particularly, SGLT-2 inhibitors have been shown to block the reabsorption of glucose from the renal filtrate in the glomerulus thereby inducing glucose excretion in the urine. As excess glucose is excreted, there is a decrease in blood glucose level, decreased hepatic storage of glucose, decreased insulin secretion and, subsequently, decreased carbohydrate conversion to fat and, ultimately, reduced accumulated fat. Selective inhibition of SGLT-2 is expected to normalize plasma glucose by enhancing glucose excretion. Consequently, SGLT-2 inhibitors provide an attractive means to improve diabetic conditions without increasing body weight or the risk of hypoglycemia. See, Isaji, M., *Current Opinion Investigational Drugs,* 8(4), 285-292 (2007). For a general review of SGLT as a therapeutic target, see also Asano, T., et al., *Drugs of the Future,* 29(5), 461-466 (2004).

Since the mode of action of SGLT-2 inhibitors is independent of insulin secretion, SGLT-2 inhibitors are associated with a low risk of hypoglycemia, which has been linked to increased cardiovascular events. Inzucchi et al., *Diabetes & Vascular Disease Research,* 12(2), 90-100 (2015). Recently, results of the effects of the SGLT-2 inhibitor, empagliflozin, in addition to the standard of care, on cardiovascular morbidity and mortality in animals with type 2 diabetes at high cardiovascular risk were published. While the results showed no significant between-group differences in the rates of myocardial infarction or stroke, in the empagliflozin group there were significantly lower rates of death from cardiovascular causes (3.7% vs. 5.9% in the placebo group; 38% relative risk reduction), hospitalization for heart failure (2.7% and 4.1%, respectively; 35% relative risk reduction), and death from any cause (5.7% and 8.3%, respectively; 32% relative risk reduction). Zinman et al., *Empagliflozin, Cardiovascular Outcomes, and Mortality in Type 2 Diabetes,* N. Engl. J. Med. 373; 22, 2117-2128 (2015). The biomarker effects of SGLT-2 inhibitors in diabetics are similar to those in non-diabetics. For example, both populations (diabetics and non-diabetics) experience increases in urinary glucose excretion and an osmotic diuretic effect. Liu et al., *Why Do SGLT-2 Inhibitors Inhibit Only 30-50% of Renal Glucose Reabsorption in Humans?,* Diabetes, 61, 2199-2204 (2012).

SUMMARY

The present invention relates to the use of certain SGLT-2 inhibitors for treating, reducing the risk and/or preventing heart failure, myocardial infarction, cardiovascular disease or cardiovascular death in animals without type 2 or type 1 diabetes.

Additionally, the present invention relates to the use of certain SGLT-2 inhibitors for treating, reducing the risk and/or preventing heart failure, myocardial infarction, cardiovascular disease or cardiovascular death in animals with type 2 or type 1 diabetes mellitus.

Additionally, the present invention relates to the use of certain SGLT-2 inhibitors for treating, reducing the risk and/or preventing heart failure, myocardial infarction, cardiovascular disease or cardiovascular death in animals with pre-diabetes.

Since the biomarker effects of SGLT-2 inhibitors in diabetics are similar to those in non-diabetics, the effects on cardiovascular morbidity and mortality in animals type 2 diabetes at high cardiovascular risk attributed to SGLT-2 inhibitors may extend to animals without type 2 diabetes but still are at high cardiovascular risk. In certain embodiments, compounds of Formula (A) and Formula (B) have been found to act as sodium-glucose cotransport (SGLT) inhibitors, may be used in the treatment, reduction of risk of and/or prevention of diseases mediated by such inhibition (e.g., heart failure, myocardial infarction, cardiovascular disease and cardiovascular death) in animals with or without type 2 or type 1 diabetes. These compounds may be represented by Formulas (A) and (B) as shown below:

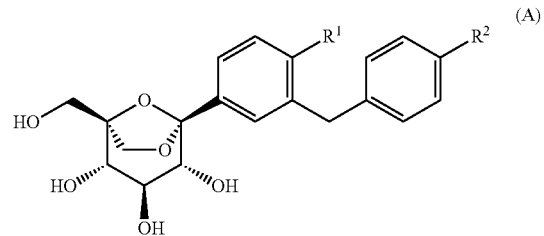

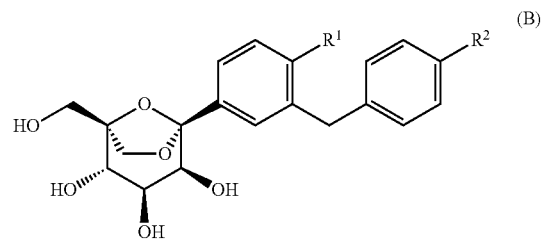

wherein R¹ is H, $(C_1-C_4)$alkyl, $(C_1-C_4)$alkoxy, Cl, F, cyano, fluoro-substituted $(C_1-C_2)$alkyl, $(C_1-C_4)$alkyl-SO$_2$—, or $(C_3-C_6)$cycloalkyl; and R² is $(C_1-C_4)$alkyl, $(C_1-C_4)$alkoxy, $(C_2-C_4)$alkynyl, 3-oxetanyloxy, 3-tetrahydrofuranyloxy, Cl, F, cyano, fluoro-substituted $(C_1-C_2)$alkyl, $(C_1-C_4)$alkyl-SO$_2$—, $(C_3-C_6)$cycloalkyl, or a $(C_5-C_6)$heterocycle having for 2 heteroatoms each independently selected from N, O, or S.

It is generally understood by those skilled in the art that various alternative substituents may be added to the compounds of Formula (A) or Formula (B) so long as the substituent(s) selected does not adversely affect the pharmacological characteristics of the compound or adversely interfere with the use of the medicament.

Specific compounds of Formula (A) include: (1S,2S,3S,4R,5S)-1-hydroxymethyl-5-[3-(4-methoxy-benzyl)-4-methyl-phenyl]-6,8-dioxa-bicyclo[3.2.1]octane-2,3,4-triol; (1S,2S,3S,4R,5S)-5-[3-(4-ethoxy-benzyl)-4-methyl-phenyl]-1-hydroxymethyl-6,8-dioxa-bicyclo[3.2.1]octane-2,3,4-triol; (1S,2S,3S,4R,5S)-5-[4-chloro-3-(4-methoxy-benzyl)-phenyl]-1-hydroxymethyl-6,8-dioxa-bicyclo[3.2.1]octane-2,3,4-triol; (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol; (1S,2S,3S,4R,5S)-5-[4-fluoro-3-(4-methoxy-benzyl)-phenyl]-1-hydroxymethyl-6,8-dioxa-bicyclo[3.2.1]octane-2,3,4-triol; 2-(4-methoxybenzyl)-4-((1S,2S,3S,4R,5S)-2,3,4-trihydroxy-1-(hydroxymethyl)-6,8-dioxa-bicyclo[3,2,1]oct-5-yl)benzonitrile; 2-(4-ethoxybenzyl)-4-((1S,2S,3S,4R,5S)-2,3,4-trihydroxy-1-(hydroxymethyl)-6,8-dioxa-bicyclo[3,2,1]oct-5-yl)benzonitrile; (1S,2S,3S,4R,5S)-5-[3-(4-ethoxy-benzyl)-4-fluoro-phenyl]-1-hydroxymethyl-6,8-dioxa-bicyclo[3.2.1]octane-2,3,4-triol; (1S,2S,3S,4R,5S)-5-{4-fluoro-3-[4-(tetrahydro-furan-3-yloxy)-benzyl]-phenyl}-1-hydroxymethyl-6,8-dioxa-bicyclo[3.2.1]octane-2,3,4-triol; (1S,2S,3S,4R,5S)-5-[3-(4-chlorobenzyl)-4-fluorophenyl]-1-hydroxymethyl-6,8-dioxabicyclo[3.2.1]octane-2,3,4-triol; (1S,2S,3S,4R,5S)-5-{4-fluoro-3-[4-(oxetan-3-yloxy)-benzyl]-phenyl}-1-hydroxymethyl-6,8-dioxa-bicyclo[3.2.1]octane-2,3,4-triol; and (1S,2S,3S,4R,5S)-5-{4-chloro-3-[4-(oxetan-3-yloxy)-benzyl]-phenyl}-1-hydroxymethyl-6,8-dioxa-bicyclo[3.2.1]octane-2,3,4-triol.

Specific compounds of Formula (B) include: (1S,2S,3S,4S,5S)-1-hydroxymethyl-5-[3-(4-methoxy-benzyl)-4-methyl-phenyl]-6,8-dioxa-bicyclo[3.2.1]octane-2,3,4-triol; (1S,2S,3S,4S,5S)-5-[3-(4-ethoxy-benzyl)-4-methyl-phenyl]-1-hydroxymethyl-6,8-dioxa-bicyclo[3.2.1]octane-2,3,4-triol; (1S,2S,3S,4S,5S)-5-[4-chloro-3-(4-methoxy-benzyl)-phenyl]-1-hydroxymethyl-6,8-dioxa-bicyclo[3.2.1]octane-2,3,4-triol; (1S,2S,3S,4S,5S)-5-[4-chloro-3-(4-ethoxy-benzyl)-phenyl]-1-hydroxymethyl-6,8-dioxa-bicyclo[3.2.1]octane-2,3,4-triol; (1S,2S,3S,4 S,5S)-5-[4-fluoro-3-(4-methoxy-benzyl)-phenyl]-1-hydroxymethyl-6,8-dioxa-bicyclo[3.2.1]octane-2,3,4-triol; (1S,2S,3S,4S,5S)-5-[3-(4-ethoxy-benzyl)-4-fluoro-phenyl]-1-hydroxymethyl-6,8-dioxa-bicyclo[3.2.1]octane-2,3,4-triol; and (1S,2S,3S,4S,5S)-5-[3-(4-chlorobenzyl)-4-fluorophenyl]-1-hydroxymethyl-6,8-dioxabicyclo[3.2.1]octane-2,3,4-triol.

In a specific embodiment of an SGTL2 inhibitor used in the methods of the present invention is a compound having the formula (4A):

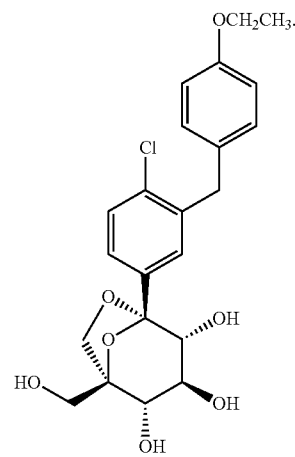

(4A)

having the chemical name (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol and described in U.S. Pat. No. 8,080,580. The compound of 4(A) is further known as ertugliflozin.

One aspect of the present invention is a method for treating a disease, disorder, or condition modulated by SGLT-2 inhibition in animals that includes the step of administering to an animal (preferably, a human) without type 2 or type 1 diabetes mellitus or pre-diabetes or administering to an animal (preferably, a human) with type 2 or type 1 diabetes mellitus or pre-diabetes, in need of such treatment a therapeutically effective amount of a compound of the present invention (or a pharmaceutical composition thereof).

One aspect of the present invention is a method for treating a cardiovascular disease, disorder, or condition modulated by SGLT-2 inhibition in animals that includes the step of administering to an animal (preferably, a human) without type 2 or type 1 diabetes mellitus or pre-diabetes or administering to an animal (preferably, a human) with type 2 or type 1 diabetes mellitus or pre-diabetes, in need of such treatment a therapeutically effective amount of a compound of the present invention (or a pharmaceutical composition thereof). Cardiovascular diseases, conditions, and/or disorders modulated by SGLT-2 inhibition include, e.g., heart failure, myocardial infarction, cardiovascular disease and cardiovascular death.

In certain embodiments the present invention is directed to a method of treating, reducing the risk of and/or preventing heart failure, myocardial infarction, cardiovascular disease or cardiovascular death in an animal comprising administering ertugliflozin or a pharmaceutically acceptable salt or a co-crystal thereof to the animal, wherein the animal has type 2 or type 1 diabetes.

In certain embodiments the present invention is directed to a method of treating, reducing the risk of and/or preventing heart failure, myocardial infarction, cardiovascular disease or cardiovascular death in an animal comprising administering ertugliflozin or a pharmaceutically acceptable salt or a co-crystal thereof to the animal, wherein the animal has pre-diabetes.

In certain embodiments the present invention is directed to a method of treating, reducing the risk of and/or preventing heart failure, myocardial infarction, cardiovascular disease or cardiovascular death in an animal comprising administering ertugliflozin or a pharmaceutically acceptable salt or a co-crystal thereof to the animal, wherein the animal does not have type 2, type 1 diabetes or pr e-diabetes.

When used herein, the expression "ertugliflozin or a pharmaceutically acceptable salt or a co-crystal thereof" includes a pharmaceutically acceptable salt of ertugliflozin as well as, a pharmaceutically acceptable salt of the co-crystal of ertugliflozin.

In certain embodiments, ertugliflozin or a pharmaceutically acceptable salt or a co-crystal thereof is administered as a pharmaceutical composition. In certain embodiments, the pharmaceutical composition comprises from 0.1 to 500 mg of ertugliflozin or a pharmaceutically acceptable salt or a co-crystal thereof, or more specifically from 1 to 200 mg, from 2 to 100 mg, or from 2 to 20 mg of ertugliflozin or a pharmaceutically acceptable salt or a co-crystal thereof. In certain embodiments, the pharmaceutical composition comprises 5 mg or 15 mg of ertugliflozin or a pharmaceutically acceptable salt or a co-crystal thereof. In certain embodiments, the pharmaceutical composition comprises 2.5 mg or 7.5 mg of ertugliflozin or a pharmaceutically acceptable salt or a co-crystal thereof. In certain embodiments, ertugliflozin or a pharmaceutically acceptable salt or a co-crystal thereof is administered once daily.

In other embodiments, the present invention is directed to a method for treating heart failure, myocardial infarction or cardiovascular disease in an animal comprising administering ertugliflozin or a pharmaceutically acceptable salt or a co-crystal thereof to the animal, wherein the animal has type 2 or type 1 diabetes.

In certain embodiments the present invention is directed to a method of reducing the risk of heart failure, myocardial infarction, cardiovascular disease or cardiovascular death in an animal comprising administering ertugliflozin or a pharmaceutically acceptable salt or a co-crystal thereof to the animal, wherein the animal has type 2 or type 1 diabetes.

In certain embodiments the present invention is directed to a method of preventing heart failure, myocardial infarction, cardiovascular disease or cardiovascular death in an animal comprising administering ertugliflozin or a pharmaceutically acceptable salt or a co-crystal thereof to the animal, wherein the animal has type 2 or type 1 diabetes.

In certain embodiments, the pharmaceutical composition comprises from 0.1 to 500 mg of ertugliflozin or a pharmaceutically acceptable salt or a co-crystal thereof, or more specifically from 1 to 200 mg, from 2 to 100 mg, or from 2 to 20 mg of ertugliflozin or a pharmaceutically acceptable salt or a co-crystal thereof. In certain embodiments, the pharmaceutical composition comprises 5 mg or 15 mg of ertugliflozin or a pharmaceutically acceptable salt or a co-crystal thereof. In certain embodiments, the pharmaceutical composition comprises 2.5 mg or 7.5 mg of ertugliflozin or a pharmaceutically acceptable salt or a co-crystal thereof. In certain embodiments, ertugliflozin or a pharmaceutically acceptable salt or a co-crystal thereof is administered once daily.

In other embodiments, the present invention is directed to a method for treating heart failure, myocardial infarction or cardiovascular disease in an animal comprising administering ertugliflozin or a pharmaceutically acceptable salt or a co-crystal thereof to the animal, wherein the animal does not have type 2 diabetes, type 1 diabetes or pre-diabetes.

In certain embodiments the present invention is directed to a method of reducing the risk of heart failure, myocardial infarction, cardiovascular disease or cardiovascular death to an animal comprising administering ertugliflozin or a pharmaceutically acceptable salt or a co-crystal thereof to the animal, wherein the animal does not have type 2 diabetes, type 1 diabetes or pre-diabetes.

In certain embodiments the present invention is directed to a method of preventing heart failure, myocardial infarction, cardiovascular disease or cardiovascular death in an animal comprising administering ertugliflozin or a pharmaceutically acceptable salt or a co-crystal thereof to the animal, wherein the animal does not have type 2 diabetes, type 1 diabetes or pre-diabetes.

In certain embodiments, the pharmaceutical composition comprises from 0.1 to 500 mg of ertugliflozin or a pharmaceutically acceptable salt or a co-crystal thereof, or more specifically from 1 to 200 mg, from 2 to 100 mg, or from 2 to 20 mg of ertugliflozin or a pharmaceutically acceptable salt or a co-crystal thereof. In certain embodiments, the pharmaceutical composition comprises 5 mg or 15 mg of ertugliflozin or a pharmaceutically acceptable salt or a co-crystal thereof. In certain embodiments, the pharmaceutical composition comprises 2.5 mg or 7.5 mg of ertugliflozin or a pharmaceutically acceptable salt or a co-crystal thereof. In certain embodiments, ertugliflozin or a pharmaceutically acceptable salt or a co-crystal thereof is administered once daily.

In other embodiments, the present invention is directed to a method for treating heart failure, myocardial infarction or cardiovascular disease in an animal comprising administering ertugliflozin or a pharmaceutically acceptable salt or a co-crystal thereof to the animal, wherein the animal has pre-diabetes.

In certain embodiments the present invention is directed to a method of reducing the risk of heart failure, myocardial infarction, cardiovascular disease or cardiovascular death in an animal comprising administering ertugliflozin or a pharmaceutically acceptable salt or a co-crystal thereof to the animal, wherein the animal has pre-diabetes.

In certain embodiments the present invention is directed to a method of preventing heart failure, myocardial infarction, cardiovascular disease or cardiovascular death in an animal comprising administering ertugliflozin or a pharmaceutically acceptable salt or a co-crystal thereof to the animal, wherein the animal has pre-diabetes.

In certain embodiments, the pharmaceutical composition comprises from 0.1 to 500 mg of ertugliflozin or a pharmaceutically acceptable salt or a co-crystal thereof, or more specifically from 1 to 200 mg, from 2 to 100 mg, or from 2 to 20 mg of ertugliflozin or a pharmaceutically acceptable salt or a co-crystal thereof. In certain embodiments, the pharmaceutical composition comprises 5 mg or 15 mg of ertugliflozin or a pharmaceutically acceptable salt or a co-crystal thereof. In certain embodiments, the pharmaceutical composition comprises 2.5 mg or 7.5 mg of ertugliflozin or a pharmaceutically acceptable salt or a co-crystal thereof. In certain embodiments, ertugliflozin or a pharmaceutically acceptable salt or a co-crystal thereof is administered once daily.

Another aspect of the present invention is a pharmaceutical composition to be used in the methods described that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include anti-obesity agents and/or anti-diabetic agents (described herein below). Also, the methods described herein include compounds described herein administered in combination with other pharmaceutical agents (in particular, anti-obesity and anti-diabetic agents described herein below). The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

In certain embodiments, the pharmaceutical composition comprises from 0.1 to 500 mg of ertugliflozin or a pharmaceutically acceptable salt or a co-crystal thereof, or more specifically from 1 to 200 mg, from 2 to 100 mg, or from 2 to 20 mg of ertugliflozin or a pharmaceutically acceptable salt or a co-crystal thereof in combination with 1 mg to 1000 mg of sitagliptin or a pharmaceutically acceptable salt thereof, or more specifically from 1 to 500 mg, from 1 to 250 mg, or from 1 to 100 mg of sitagliptin or a pharmaceutically acceptable salt thereof. In certain embodiments, the methods described herein include administering 5 mg or 15 mg of ertugliflozin or a pharmaceutically acceptable salt or a co-crystal thereof in combination with 25 mg, 50 mg or 100 mg of sitagliptin or a pharmaceutically acceptable salt thereof. In other embodiments, the methods described herein include administering 2.5 mg or 7.5 mg of ertugliflozin or a pharmaceutically acceptable salt or a co-crystal thereof in combination with 25 mg, 50 mg or 100 mg of sitagliptin or a pharmaceutically acceptable salt thereof.

In certain embodiments, the pharmaceutical composition comprises from 0.1 to 500 mg of ertugliflozin or a pharmaceutically acceptable salt or a co-crystal thereof, or more specifically from 1 to 200 mg, from 2 to 100 mg, or from 2 to 20 mg of ertugliflozin or a pharmaceutically acceptable salt or a co-crystal thereof in combination with 0.01 mg to 2000 mg of metformin or a pharmaceutically acceptable salt thereof, or more specifically from 1 to 2000 mg, from 500 to 2000 mg, or from 1000 to 2000 mg of metformin or a pharmaceutically acceptable salt thereof. In certain embodiments, the methods described herein include administering 5 mg or 15 mg of ertugliflozin or a pharmaceutically acceptable salt or a co-crystal thereof in combination with 1000 mg, 1700 mg or 2000 mg of metformin, or a pharmaceutically acceptable salt thereof. In certain embodiments, the methods described herein include administering 2.5 mg or 7.5 mg of ertugliflozin or a pharmaceutically acceptable salt or a co-crystal thereof in combination with 1000 mg, 1700 mg or 2000 mg of metformin, or a pharmaceutically acceptable salt thereof.

In still other embodiments, the pharmaceutical composition comprises from 0.1 to 500 mg of ertugliflozin or a pharmaceutically acceptable salt or a co-crystal thereof, or more specifically from 1 to 200 mg, from 2 to 100 mg, or from 2 to 20 mg of ertugliflozin or a pharmaceutically acceptable salt or a co-crystal thereof in combination with 1 mg to 1000 mg of sitagliptin or a pharmaceutically acceptable salt thereof, or more specifically from 1 to 500 mg, from 1 to 250 mg, or from 1 to 100 mg of sitagliptin or a pharmaceutically acceptable salt thereof, and 0.01 mg to 2000 mg of metformin or a pharmaceutically acceptable salt thereof, or more specifically from 1 to 2000 mg, from 500 to 2000 mg, or from 1000 to 2000 mg of metformin or a pharmaceutically acceptable salt thereof. In certain embodiments, the methods described herein include administering 5 mg or 15 mg of ertugliflozin or a pharmaceutically acceptable salt or a co-crystal thereof in combination with 25 mg, 50 mg or 100 mg of sitagliptin or a pharmaceutically acceptable salt thereof and 1000 mg, 1700 mg or 2000 mg of metformin, or a pharmaceutically acceptable salt thereof. In certain embodiments, the methods described herein include administering 2.5 mg or 7.5 mg of ertugliflozin or a pharmaceutically acceptable salt or a co-crystal thereof in combination with 25 mg, 50 mg or 100 mg of sitagliptin or a pharmaceutically acceptable salt thereof and 1000 mg, 1700 mg or 2000 mg of metformin, or a pharmaceutically acceptable salt thereof.

In certain embodiments, the pharmaceutical composition comprises from 0.1 to 500 mg of ertugliflozin or a pharmaceutically acceptable salt or a co-crystal thereof, or more specifically from 1 to 200 mg, from 2 to 100 mg, or from 2 to 20 mg of ertugliflozin or a pharmaceutically acceptable salt or a co-crystal thereof in combination with 1 mg to 10 mg of a sulfonylurea (SU) or a pharmaceutically acceptable salt thereof, or more specifically from 1 to 8 mg, from 1 to 6 mg, or from 1 to 2 mg of a sulfonylurea (SU) or a pharmaceutically acceptable salt thereof. In certain embodiments, the methods described herein include administering 5 mg or 15 mg of ertugliflozin or a pharmaceutically acceptable salt or a co-crystal thereof in combination with 1 mg, 2 mg or 8 mg of a sulfonylurea (SU) or a pharmaceutically acceptable salt thereof. In other embodiments, the methods described herein include administering 2.5 mg or 7.5 mg of ertugliflozin or a pharmaceutically acceptable salt or a co-crystal thereof in combination with 1 mg, 2 mg or 8 mg of a sulfonylurea (SU) or a pharmaceutically acceptable salt thereof.

It is to be understood that both the foregoing general description and the following detailed description are exemplary and explanatory only and are not restrictive of the invention, as claimed.

DETAILED DESCRIPTION

The present invention may be understood even more readily by reference to the following detailed description of exemplary embodiments of the invention and the examples included therein.

Before the present methods are disclosed and described, it is to be understood that this invention is not limited to specific synthetic methods of making the disclosed compounds, or compositions of use therein, that may of course vary. It is also to be understood that the terminology used herein is for the purpose of describing particular embodiments only and is not intended to be limiting. The plural and singular should be treated as interchangeable, other than the indication of number.

As used herein, the term "alkyl" refers to a hydrocarbon radical of the general formula $C_nH_{2(n+1)}$. The alkane radical may be straight or branched. For example, the term "($C_1$-$C_6$)alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, alkylsulfonyl, and alkylthio group have the same definition as above. When indicated as being "optionally substituted", the alkane radical or alkyl moiety may be unsubstituted or substituted with one or more substituents (generally, one to three substituents except in the case of halogen substituents where it means a complete substitution of halogen for hydrogen such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoroethyl, 1,1-difluoroethyl and the like).

The term "cycloalkyl" refers to nonaromatic rings and may exist as a single ring, bicyclic ring or a spiro ring. Unless specified otherwise, the carbocyclic ring is generally a 3- to 8-membered ring. For example, cycloalkyl include groups such as cyclopropyl, cyclobutyl, cyclopentyl, cyclohexyl, cyclohexenyl, norbornyl (bicyclo[2.2.1]heptyl), bicyclo[2.2.2]octyl, and the like.

The term "heterocycle" refers to nonaromatic rings and may exist as a single ring, bicyclic ring or a spio ring. Unless specified otherwise, the heterocyclic ring is generally a 3- to 6-membered ring containing 1 to 3 heteroatoms (preferably 1 or 2 heteroatoms) independently selected from sulfur, oxygen and/or nitrogen. Heterocyclic rings include groups such as epoxy, aziridinyl, tetrahydrofuranyl, pyrrolidinyl, N-methylpyrrolidinyl, piperidinyl, piperazinyl, pyrazolidinyl, 4H-pyranyl, morpholino, thiomorpholino, tetrahydrothienyl, tetrahydrothienyl 1,1-dioxide, and the like.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents, reduces the risk of, or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. In specific embodiments herein, animal refers to humans.

The phrase "pharmaceutically acceptable" indicates that the substance or composition must be compatible chemically and/or toxicologically, with the other ingredients within a formulation, and/or the mammal being treated therewith.

The terms "treating", "treat", or "treatment" refers to the management and care of an animal, in particular, the attenuation, amelioration, or elimination of one or more symptoms of a particular disease, condition, or disorder.

The terms "modulated" or "modulating", or "modulate(s)", as used herein, unless otherwise indicated, refers to the inhibition of the sodium-glucose transporter (in particular, SGLT-2) with compounds of the present invention thereby partially or fully preventing glucose transport across the transporter.

The term "preventing", as used herein, unless otherwise indicated, refers to thwarting or stopping the occurrence of a cardiovascular event, such as heart failure, myocardial infarction, or cardiovascular death, or thwarting or stopping the onset of cardiovascular disease.

The phrase "reduce the risk", as used herein, unless indicated, refers to reducing the likelihood or severity of a cardiovascular event, such as heart failure, myocardial infarction, or cardiovascular death, or reducing the likelihood or severity of cardiovascular disease.

The terms "compounds" or "compounds of the present invention" (unless specifically identified otherwise) refer to compounds of Formula (A), Formula (B) and all pure and mixed stereoisomers (including diastereoisomers and enantiomers), tautomers and isotopically labeled compounds.

Hydrates and solvates of the compounds of the present invention are considered compositions of the present invention, wherein the compound is in association with water or solvent, respectively. The compounds may also exist in one or more crystalline states, i.e. as co-crystals, polymorphs, or they may exist as amorphous solids.

In one embodiment, in Formula (A) or (B), $R^1$ is H, methyl, ethyl, propyl, isopropyl, methoxy, ethoxy, F, Cl, cyano, —$CF_3$, cyclopropyl, or cyclobutyl. In another embodiment, $R^1$ is H, methyl, ethyl, isopropyl, methoxy, ethoxy, F, Cl, cyano, —$CF_3$, or cyclopropyl. In a further embodiment, $R^1$ is H, methyl, ethyl, methoxy, ethoxy, F, Cl, cyano, —$CF_3$, or cyclopropyl. In yet a further embodiment, $R^1$ is methyl, ethyl, F, Cl, cyano, $CF_3$, or cyclopropyl.

In one embodiment, $R^2$ is methyl, ethyl, propyl, isopropyl, methoxy, ethoxy, F, Cl, cyano, —$CF_3$, —$CF_2CH_3$, ethynyl, 3-oxetanyloxy, 3-tetrahydrofuranyloxy, or cyclopropyl. In another embodiment, $R^2$ is methyl, ethyl, isopropyl, methoxy, ethoxy, F, Cl, cyano, —$CF_3$, —$CF_2CH_3$, ethynyl, 3-oxetanyloxy, 3-tetrahydrofuranyloxy, or cyclopropyl. In a further embodiment, $R^2$ is methyl, ethyl, methoxy, ethoxy, F, Cl, cyano, —$CF_3$, —$CF_2CH_3$, ethynyl, 3-oxetanyloxy, 3-tetrahydrofuranyloxy, or cyclopropyl. In yet a further embodiment, $R^2$ is methoxy or ethoxy.

"Ertugliflozin" means the compound of formula (4A):

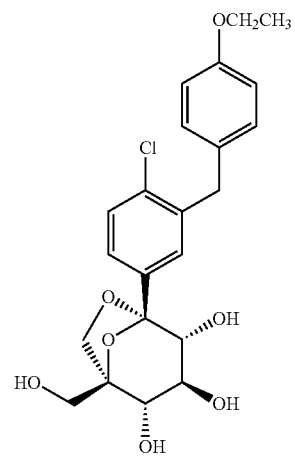

4A having the chemical name (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol. In certain embodiments of the methods described herein ertugliflozin can exist as a co-crystal or a pharmaceutically acceptable salt.

In one embodiment, the co-crystal comprises the compound 4A and L-proline or L-pyroglutamic acid.

In a further embodiment, the co-crystal has one or more of the following:
  a) space group of P2(1)2(1)2(1) and unit cell parameters substantially equal to the following:
     a=7.4907(10) Å α=90°.
     b=12.8626(15) Å β=90°.
     c=28.029(4) Å γ=90°;
  b) a powder x-ray diffraction pattern comprising 2-theta values of (CuKα radiation, wavelength of 1.54056 Å) 6.4±0.2, 16.7±0.2, 17.4±0.2 and 21.1±0.2;
  c) a solid state 13C NMR spectrum having peak positions at 16.5±0.2, 131.1±0.2, 158.7±0.2, and 181.5±0.2 ppm as determined on a 500 MHz spectrometer relative to crystalline adamantine of 29.5 ppm; or d) a differential scanning calorimetry thermogram having an endotherm of about 142.5±2° C.

In a further embodiment, the crystal is a co-crystal comprising the compound of formula (4A) and L-pyroglutamic acid in a 1:1 stochiometric ratio.

Compounds used in the methods of the present invention may be synthesized by synthetic routes that include processes analogous to those well-known in the chemical arts, particularly in light of the description contained herein. The starting materials are generally available from commercial sources such as Aldrich Chemicals (Milwaukee, WI) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality of intermediates may be necessary. The need for such protection will vary depending on the nature of the remote functionality and the conditions of the preparation methods. A "hydroxy-protecting group" refers to a substituent of a hydroxy group that blocks or protects the hydroxy functionality. Suitable hydroxyl-protecting groups (O-Pg) include for example, allyl, acetyl (Ac), silyl (like trimethylsilyl (TMS) or tert-butyldimethylsilyl (TBS)), benzyl (Bn), para-methoxybenzyl (PMB), trityl (Tr), para-bromobenzoyl, para-nitrobenzoyl and the like (e.g. benzylidene for protection of 1,3-diols). The need for such protection is readily determined by one skilled in the art. For a general description of protecting groups and their use, see T. W. Greene, *Protective Groups in Organic Synthesis*, John Wiley & Sons, New York, 1991.

Scheme 1 outlines the general procedures one could use to provide compounds of the present invention.

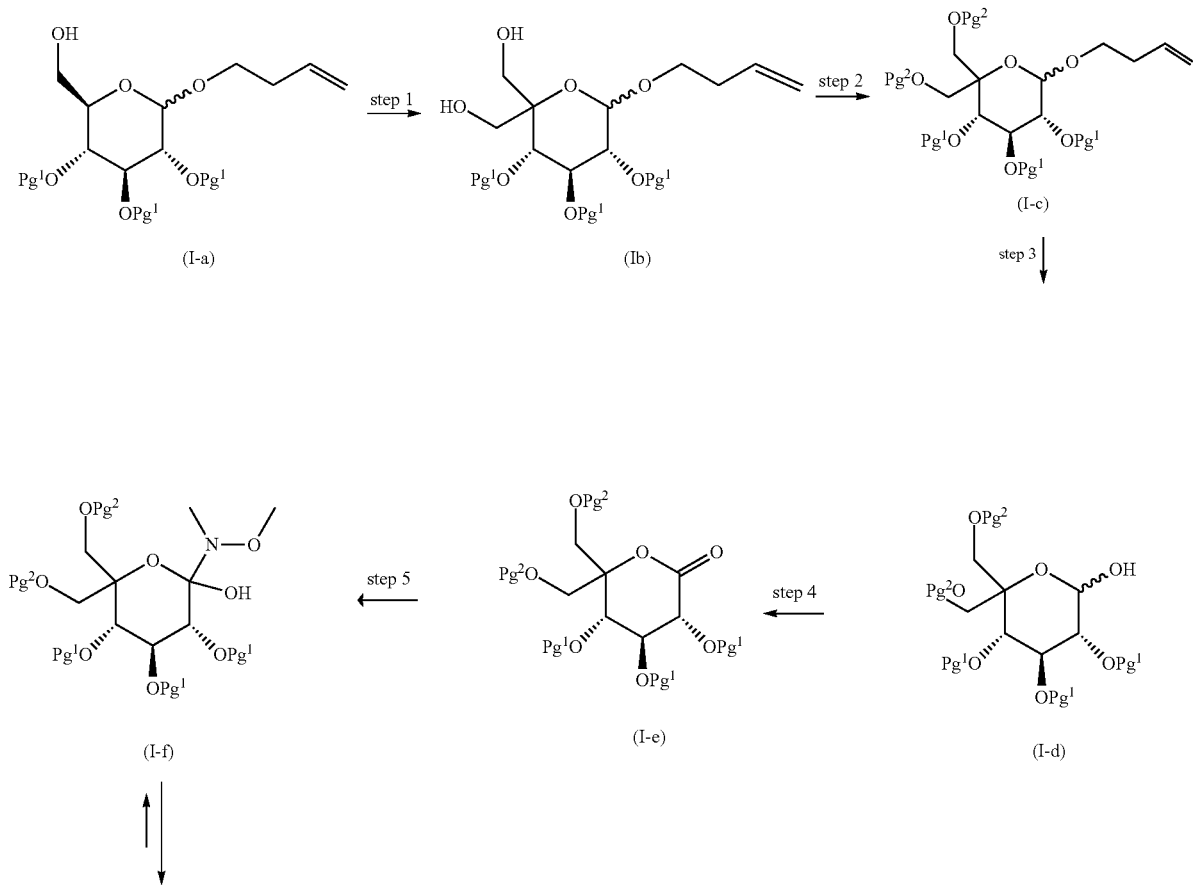

-continued

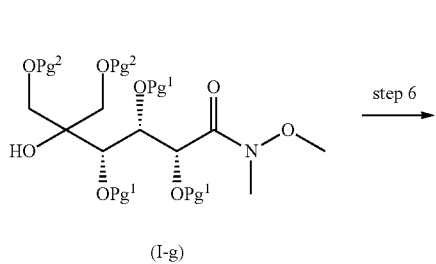

(I-g)

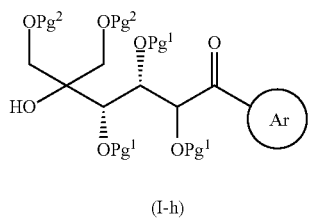

(I-h)

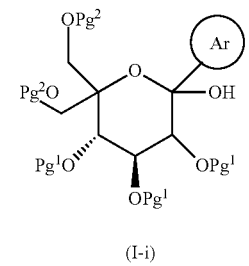

(I-i)

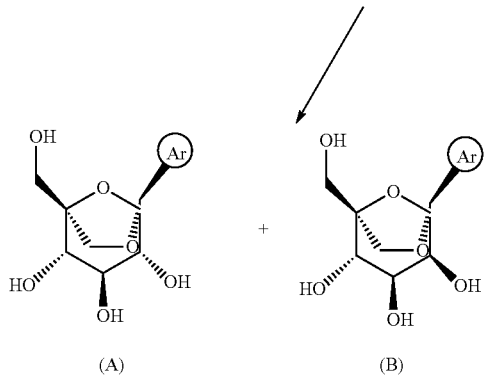

(A)    (B)

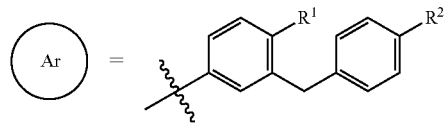

Allyl 2,3,4-tri-O-benzyl-D-glucopyranoside (I-a, where Pg¹ is a benzyl group) can be prepared by procedures described by Shinya Hanashima, et al., in *Bioorganic & Medicinal Chemistry*, 9, 367 (2001); Patricia A. Gent et al. in *Journal of the Chemical Society, Perkin* 1, 1835 (1974); Hans Peter Wessel in the *Journal of Carbohydrate Chemistry*, 7, 263, (1988); or Yoko Yuasa, et al., in *Organic Process Research & Development*, 8, 405-407 (2004). In step 1 of Scheme 1, the hydroxymethylene group can be introduced onto the glycoside by means of a Swern oxidation followed by treatment with formaldehyde in the presence of an alkali metal hydroxide (e.g., sodium hydroxide). This is referred to as an aldol-Cannizzaro reaction. The Swern oxidation is described by Kanji Omura and Daniel Swern in *Tetrahedron*, 34, 1651 (1978). Modifications of this process known to those of skill in the art may also be used. For example, other oxidants, like stabilized 2-iodoxybenzoic acid described by Ozanne, A. et al. in *Organic Letters*, 5, 2903 (2003), as well as other oxidants known by those skilled in the art can also be used. The aldol Cannizzaro sequence has been described by Robert Schaffer in the *Journal of The American Chemical Society*, 81, 5452 (1959) and Amigues, E. J., et al., in *Tetrahedron*, 63, 10042 (2007).

In step 2 of Scheme 1, protecting groups (Pg²) can be added by treating intermediate (I-b) with the appropriate reagents and procedures for the particular protecting group desired. For example, p-methoxybenzyl (PMB) groups may be introduced by treatment of intermediate (I-b) with p-methoxybenzyl bromide or p-methoxybenzyl chloride in the presence of sodium hydride, potassium hydride, potassium tert-butoxide in a solvent like tetrahydrofuran, 1,2-dimethoxyethane or N,N-dimethylformamide (DMF). Conditions involving para-methoxybenzyltrichloroacetimidate in presence of a catalytic amount of acid (e.g., trifluoromethanesulfonic acid, methanesulfonic acid, or camphorsulfonic acid) in a solvent such as dichloromethane, heptane or hexanes can also be used. Benzyl (Bn) groups may be introduced by treatment of intermediate (I-b) with benzyl bromide or benzyl chloride in the presence of sodium hydride, potassium hydride, potassium tert-butoxide in a solvent like tetrahydrofuran, 1,2-dimethoxyethane or N, N-dimethylformamide. Conditions involving benzyltrichloroacetimidate in presence of a catalytic amount of acid (e.g., trifluoromethanesulfonic acid, methanesulfonic acid, or camphorsulfonic acid) in a solvent such as dichloromethane, heptane or hexanes can also be used.

In step 3 of Scheme 1, the allyl protection group is removed (e.g., by treatment with palladium chloride in methanol; cosolvent like dichloromethane may also be used; other conditions known by those skilled in the art could also be used, see T. W. Greene, *Protective Groups in Organic Synthesis*, John Wiley & Sons, New York, 1991) to form the lactol (I-d). In step 4 of Scheme 1, oxidation of the unprotected hydroxyl group to an oxo group (e.g., Swern oxidation) then forms the lactone (I-e).

In step 5 of Scheme 1, the lactone (I-e) is reacted with N, O-dimethyl hydroxylamine hydrochloride to form the corresponding Weinreb amide which may exist in equilibrium in a closed/opened form. (I-f/I-g). The "Weinreb amide" (I.g) can be made using procedures well known to those of skill in the art. See, Nahm, S., and S. M. Weinreb, *Tetrahedron Letters*, 22 (39), 3815-1818 (1981). For example, intermediate (I-f/I-g) can be prepared from the commercially available N, O-dimethylhydroxylamine hydrochloride and an activating agent (e.g., trimethylaluminum).

In step 6 of Scheme 1, the aryl benzyl group (Ar) is introduced using the desired organometallic reagent (e.g., organo lithium compound (ArLi) or organomagnesium compound (ArMgX)) in tetrahydrofuran (THF) at a temperature ranging from about −78° C. to about 20° C. followed by hydrolysis (upon standing in protic conditions) to the corresponding lactol which may be in equilibrium with the corresponding ketone (I-h). The bridged ketal motif found in (A) and (B) can be prepared by removing the protecting groups ($Pg^2$) using the appropriate reagents for the protecting groups employed. For example, the, p-methoxybenzyl (PMB) protecting groups may be removed by treatment with trifluoroacetic acid in the presence of anisole and dichloromethane (DCM) at about 0° C. to about 23° C. (room temperature). The remaining protecting groups ($Pg^1$) may then be removed using the appropriate chemistry for the particular protecting groups. For example, benzyl protecting groups may be removed by treating with formic acid in the presence of palladium (Pd black) in a protic solvent (e.g., ethanol/THF) at about room temperature to produce the final products (A) and (B). When $R^1$ is CN, the use of a Lewis acid like boron trichloride at a temperature ranging from about −78° C. to about room temperature in a solvent like dichloromethane or 1,2-dichloroethane may also be used to remove benzyl protective and/or para-methoxybenzyl protective groups.

When $R^1$ is CN and $R^2$ is ($C_1$-$C_4$)alkoxy in intermediate (I-i) or in products (A) or (B), upon treatment with a Lewis acid such as boron trichloride or boron tribromide, partial to complete de-alkylation to the corresponding phenol may occur to lead to the corresponding compound (A) or (B) where $R^1$ is CN and $R^2$ is OH. If this occurs, the ($C_1$-$C_4$) alkoxy group may be re-introduced via selective alkylation using a ($C_1$-$C_4$) alkyl iodide under mildly basic conditions, for example, potassium carbonate in acetone at a temperature ranging from about room temperature to about 56 degrees Celsius.

When $R^1$ and/or $R^2$ is ($C_1$-$C_4$)alkyl-$SO_2$— it is understood by one skilled in the art that the organometallic addition step 6 (Scheme 1) will be carried out on the corresponding ($C_1$-$C_4$)alkyl-S— containing organometallic reagent. The thio-alkyl is then oxidized at a later stage to the corresponding sulfone using conventional methods known by those skilled in the art.

The compounds of the present invention may be prepared as co-crystals using any suitable method. A representative scheme for preparing such co-crystals is described in Scheme 2.

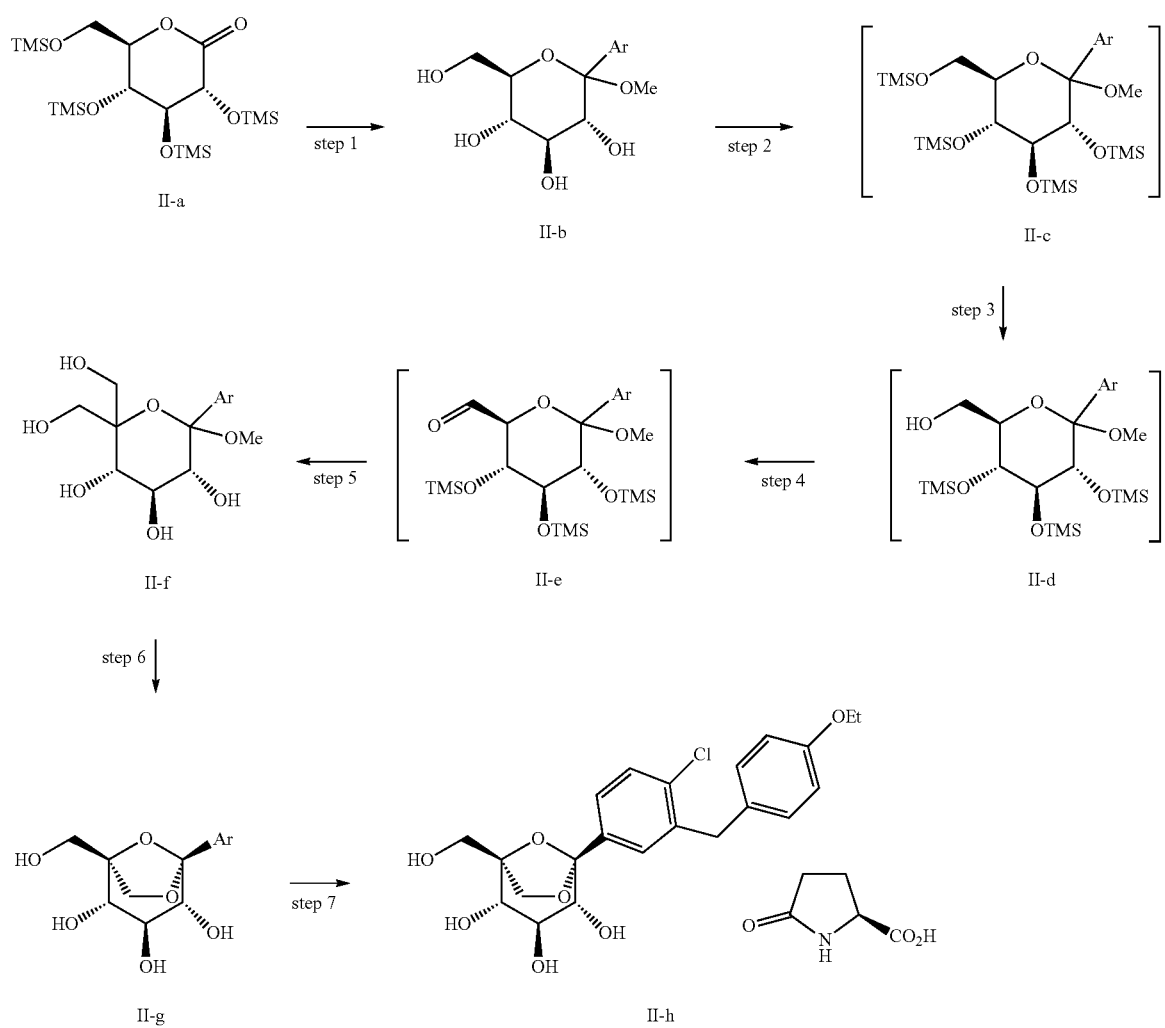

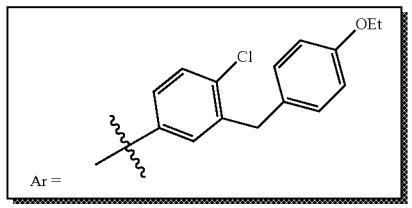

Ar =

In Scheme 2, wherein Me is methyl and Et is ethyl, in step 1, 1-(5-bromo-2-chlorobenzyl)-4-ethoxybenzene is dissolved in 3:1, toluene:tetrahydrofuran followed by cooling the resulting solution to <−70° C. To this solution is added hexyllithium while maintaining the reaction at ≤−65° C. followed by stirring for 1 hour. (3R,4S,5R,6R)-3,4,5-tris(trimethylsilyloxy)-6-((trimethylsilyloxy)methyl)-tetrahydropyran-2-one (II-a) is dissolved in toluene and the resulting solution is cooled to −15° C. This solution is then added to the −70° C. aryllithium solution followed by stirring for 1 hour. A solution of methanesulfonic acid in methanol is then added followed by warming to room temperature and stirring for 16 to 24 hours. The reaction is deemed complete when the α-anomer level is ≤3%. The reaction is then basified by the addition of 5 M aqueous sodium hydroxide solution. The resulting salts are filtered off followed by concentration of the crude product solution. 2-methyltetrahydrofuran is added as a co-solvent and the organic phase is extracted twice with water. The organic phase is then concentrated to 4 volumes in toluene. This concentrate is then added to a 5:1, heptane:toluene solution causing precipitate to form. The solids are collected and dried under vacuum to afford a solid.

In step 2 of Scheme 2, to (II-b) in methylene chloride is added imidazole followed by cooling to 0° C. and then addition of trimethylsilylchloride to give the persilylated product. The reaction is warmed to room temperature and quenched by the addition of water, and the organic phase is washed with water. This crude methylene chloride solution of (II-c) is dried over sodium sulfate and then taken on crude into the next step.

In step 3 of Scheme 2, the crude solution of (II-c) in methylene chloride is concentrated to low volume and then the solvent is exchanged to methanol. The methanol solution of (II-c) is cooled to 0° C., then 1 mol % of potassium carbonate is added as a solution in methanol followed by stirring for 5 hours. The reaction is then quenched by addition of 1 mol % acetic acid in methanol, followed by warming to room temperature, solvent exchange to ethyl acetate, and then filtration of the minor amount of inorganic solids. The crude ethyl acetate solution of (II-d) is taken directly into the next step.

In step 4 of Scheme 2, the crude solution of (II-d) is concentrated to low volume, then diluted with methylene chloride and dimethylsulfoxide. Triethylamine is added followed by cooling to 10° C. and then sulfur trioxide pyridine complex is added in 3 portions as a solid at 10 minute intervals. The reaction is stirred an additional 3 hours at 10° C. before quenching with water and warming to room temperature. The phases are separated followed by washing the methylene chloride layer with aqueous ammonium chloride. The crude methylene chloride solution of (II-e) is taken directly into the next step.

In step 5 of Scheme 2, the crude solution of (II-e) is concentrated to low volume and then the solvent is exchanged to ethanol. Thirty equivalents of aqueous formaldehyde is added followed by warming to 55° C. An aqueous solution of 2 equivalents of potassium phosphate, tribasic is added followed by stirring for 24 hours at 55° C. The reaction temperature is then raised to 70° C. for an additional 12 hours. The reaction is cooled to room temperature, diluted with tert-butyl methyl ether and brine. The phases are separated followed by solvent exchange of the organic phase to ethyl acetate. The ethyl acetate phase is washed with brine and concentrated to low volume. The crude concentrate is then purified by silica gel flash chromatography eluting with 5% methanol, 95% toluene. Product containing fractions are combined and concentrated to low volume. Methanol is added followed by stirring until precipitation occurs. The suspension is cooled and the solids are collected and rinsed with heptane followed by drying. Product (II-f) is isolated as a solid.

In step 6 of Scheme 2, compound (II-f) is dissolved in 5 volumes of methylene chloride followed by the addition of 1mol % SiliaBond® tosic acid and stirring for 18 hours at room temperature. The acid catalyst is filtered off and the methylene chloride solution of (II-g) is taken directly into the next step co-crystallization procedure.

In step 7 of Scheme 2, the methylene chloride solution of (II-g) is concentrated and then the solvent is exchanged to 2-propanol. Water is added followed by warming to 55° C. An aqueous solution of L-pyroglutamic acid is added followed by cooling the resulting solution to room temperature. The solution is then seeded and granulated for 18 hours. After cooling, the solids are collected and rinsed with heptane followed by drying. Product (II-h) is isolated as a solid.

An alternative synthesis route for compounds (A) of the present invention is depicted in Scheme 3 and described below.

Scheme 3

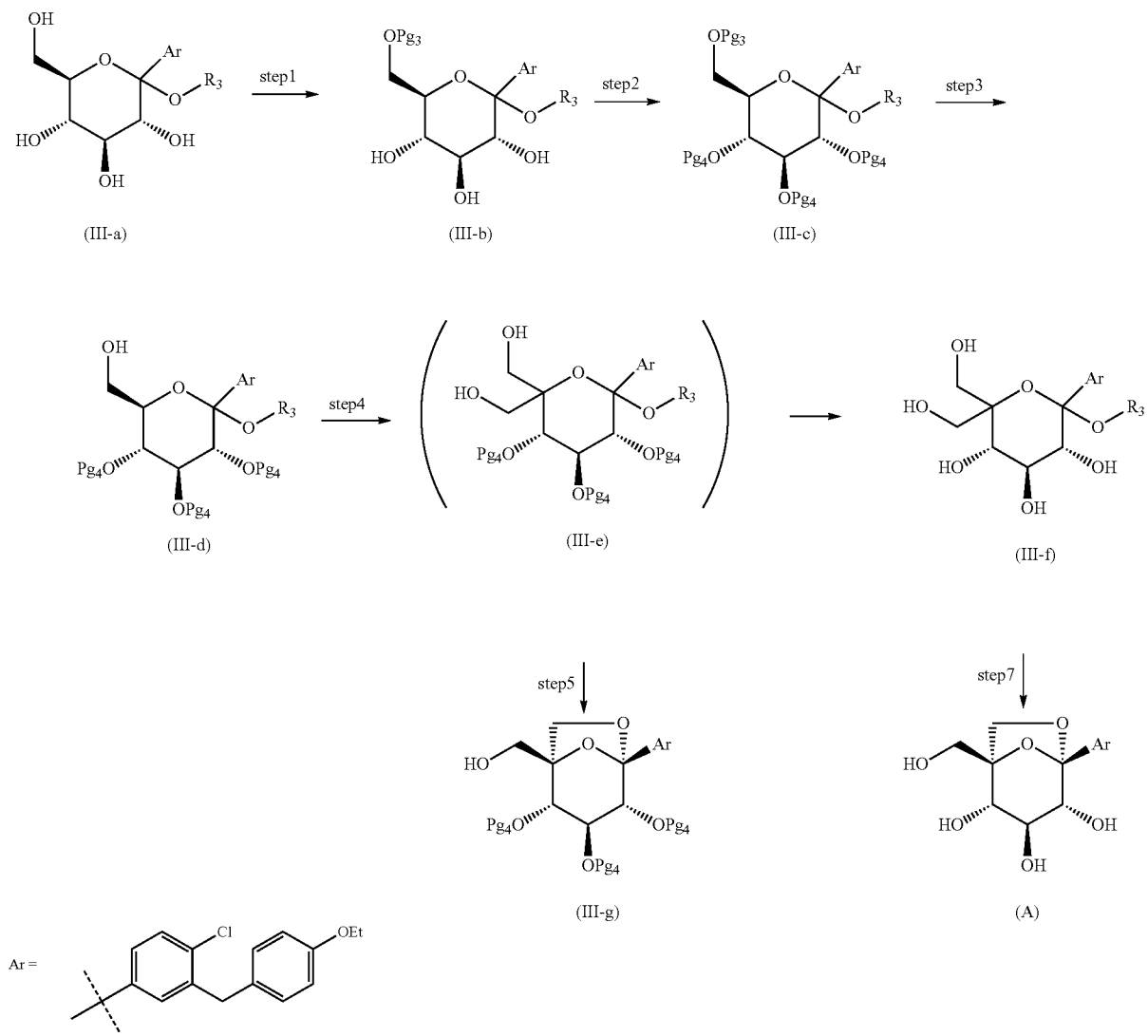

The synthesis of (III-a), where $R_3$ is an alkyl or fluoro substituted alkyl (except for the carbon adjacent to the oxygen atom) can be prepared in a similar way as described in step 1 of Scheme 2. In step 1 of Scheme 3, the primary hydroxyl group is selectively protected by an appropriate protective group. For example, a trityl group ($Pg_3$=Tr) can be introduced by treatment of intermediate (III-a) with chlorotriphenylmethane in presence of a base like pyridine in a solvent like toluene, tetrahydrofuran or dichloromethane at a temperature ranging from about 0 degrees Celsius to about room temperature. Additional examples of such protective groups and experimental conditions are known by those skilled in the art and can be found in T. W. Greene, *Protective Groups in Organic Synthesis*, John Wiley & Sons, New York, 1991. In step 2 of Scheme 3, the secondary hydroxyl groups can be protected by the appropriate protecting groups. For example, benzyl groups ($Pg_4$ is Bn) can be introduced by treatment of intermediate (III-b) with benzyl bromide or benzyl chloride in the presence of sodium hydride, potassium hydride, potassium tert-butoxide in a solvent like tetrahydrofuran, 1,2-dimethoxyethane or N,N-dimethylformamide at a temperature ranging from about 0 degrees Celsius to about 80 degrees Celsius. Acetyl or benzoyl groups ($Pg_4$=Ac or Bz) may be introduced by treatment of intermediate (III-b) with acetyl chloride, acetyl bromide or acetic anhydride, benzoyl chloride or benzoic anhydride in the presence of a base like triethylamine, N,N-diisopropylethylamine or 4-(dimethylamino)pyridine in a solvent like tetrahydrofuran, 1,2-dimethoxyethane or dichloromethane at a temperature ranging from about 0 degrees Celsius to about 80 degrees Celsius.

In step 3 of Scheme 3, the primary hydroxyl group is deprotected to lead to intermediate (III-d). When $Pg_3$ is Tr, intermediate (III-c) is treated in the presence of an acid like para-toluenesulfonic acid in an alcoholic solvent like methanol at a temperature ranging from about −20 degrees Celsius to about room temperature to provide intermediate (III-d). Cosolvents like chloroform may be used.

In step 4 of Scheme 3, a hydroxymethylene group is introduced through a process similar to the one already described in Scheme 1 (step 1) and Scheme 2 (steps 4 and 5). Other sources of formaldehyde, like paraformaldehyde in a solvent like ethanol at a temperature ranging from about room temperature to about 70 degrees Celsius in the presence of an alkali metal alkoxide can also be used in this step. When Pg$_4$ is Bn, this step provides intermediate (III-e) and when Pg$_4$ is Ac or Bz, this step provides intermediate (III-f).

In step 5 of Scheme 3, intermediate (III-e) is treated with an acid like trifluoroacetic acid or an acidic resin in a solvent like dichloromethane at a temperature ranging from about −10 degrees Celsius to about room temperature to produce intermediate (III-g).

In step 6 of Scheme 3, the remaining protecting groups (Pg$_4$) may then be removed using the appropriate chemistry for the particular protecting groups. For example, benzyl protecting groups may be removed by treating with formic acid in the presence of palladium (Pd black) in a protic solvent (e.g., ethanol/THF) at about room temperature to produce the final product (A).

In step 7 of Scheme 3, intermediate (III-f) is treated with an acid like trifluoroacetic acid or an acidic resin in a solvent like dichloromethane at a temperature ranging from about −10 degrees Celsius to about room temperature to produce the final product (A).

Another alternative scheme for synthesizing product (A) is depicted in Scheme 4 and described below.

Scheme 4

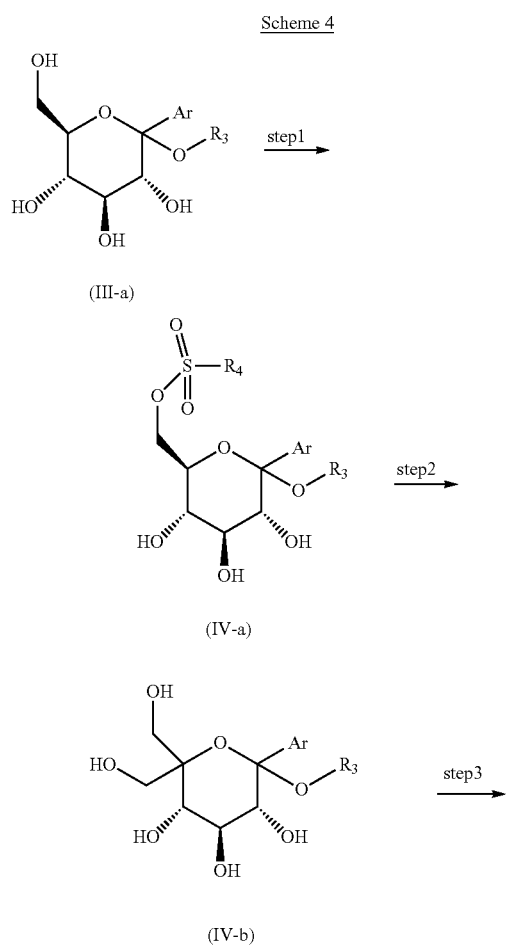

(III-a)

(IV-a)

(IV-b)

-continued

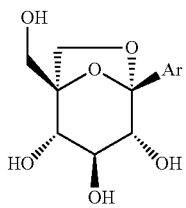

(A)

Ar = 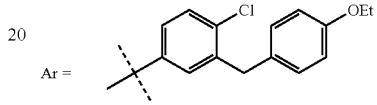

In step 1 of Scheme 4, intermediate (III-a) is treated with the appropriate arylsulfonyl chloride R$_4$SO$_2$Cl or arylsulfonic anhydride R$_4$S(O)$_2$OS(O)$_2$R$_4$ (wherein R$_4$ is an optionally substituted aryl group, such as found in the arylsulfonyl chlorides 4-methyl-benzenesulfonyl chloride, 4-nitro-benzenesulfonyl chloride, 4-fluoro-benzenesulfonyl chloride, 2,6-dichloro-benzenesulfonyl chloride, 4-fluoro-2-methyl-benzenesulfonyl chloride, and 2,4,6-trichloro-benzenesulfonyl chloride, and in the arylsulfonic anhydride, p-toluenesulfonic anhydride) in presence of a base like pyridine, triethylamine, N,N-diisopropylethylamine in a solvent like tetrahydrofuran, 2-methyltetrahydrofuran at a temperature ranging from about −20 degrees Celsius to about room temperature. Some Lewis acids like zinc(II) bromide may be used as additives.

In step 2 of Scheme 4, intermediate (IV-a) is submitted to a Kornblum-type oxidation (see, Kornblum, N., et al., *Journal of The American Chemical Society*, 81, 4113 (1959)) to produce the corresponding aldehyde which may exist in equilibrium with the corresponding hydrate and/or hemiacetal form. For example intermediate (IV-a) is treated in the presence of a base like pyridine, 2,6-lutidine, 2,4,6-collidine, N,N-diisopropylethylamine, 4-(dimethylamino)pyridine in a solvent like dimethyl sulfoxide at a temperature ranging from about room temperature to about 150 degrees Celsius. The aldehyde intermediate produced is then submitted to the aldol/Cannizzaro conditions described for step 1 (Scheme 1) and step 5 (Scheme 2) to produce intermediate (IV-b).

In step 3 of Scheme 4, intermediate (IV-b) is treated with an acid like trifluoroacetic acid or an acidic resin in a solvent like dichloromethane at a temperature ranging from about −10 degrees Celsius to about room temperature to produce the final product (A). When R$^2$ is (C$_2$-C$_4$)alkynyl the process may be performed using Scheme 5, wherein R$^6$ is H or (C$_1$-C$_2$)alkyl.

Scheme 5
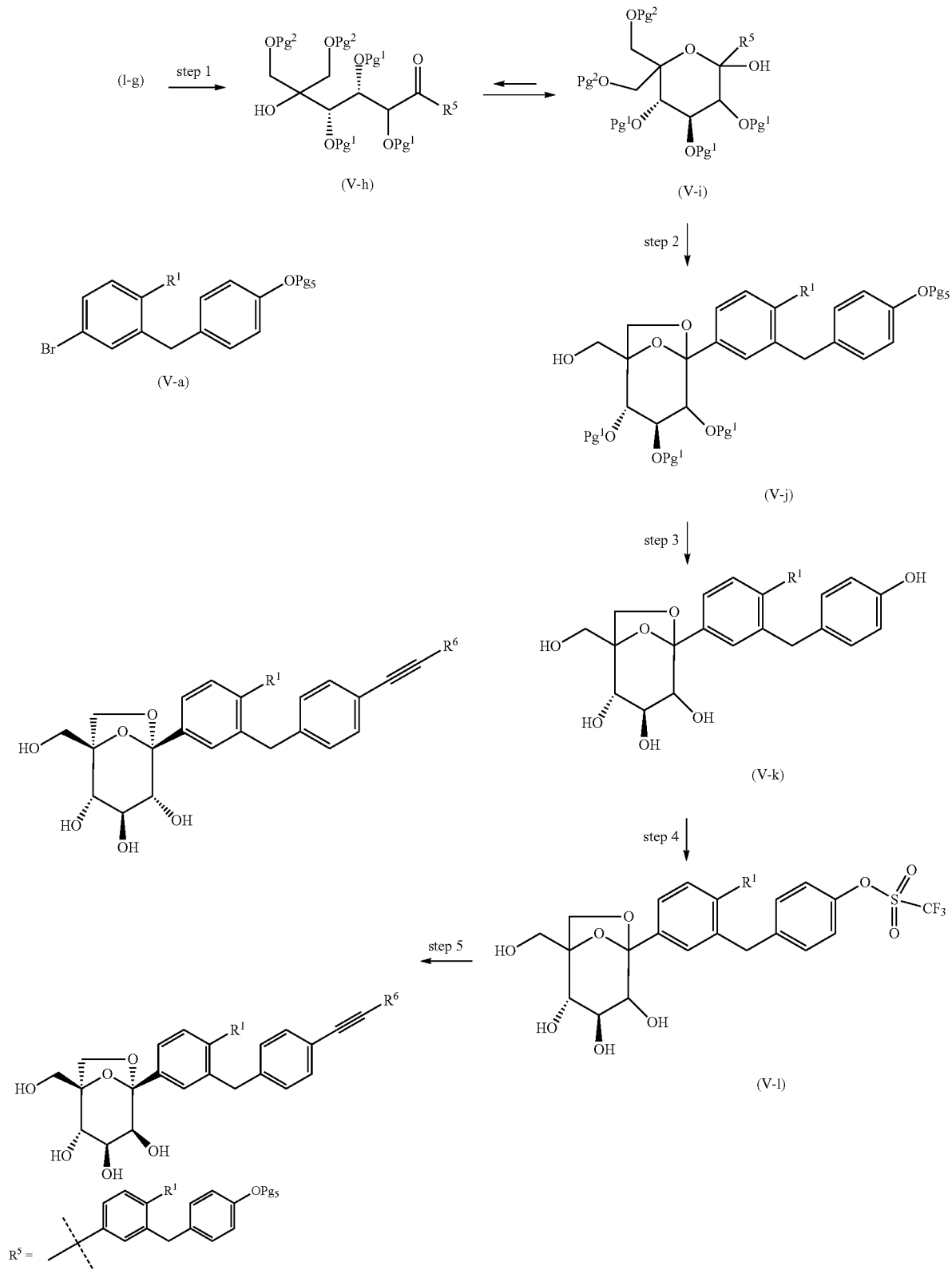
In step 1 of Scheme 5, which provides intermediate (V-i), the organometallic addition step is carried out in a similar way to the one described in Scheme 1, step 6, using the organometallic reagent derived from (V-a), where $Pg_5$ is a suitable protective group for the hydroxyl group. For instance Pg$_5$ can be a tert-butyldimethylsilyl group (TBS) (see US2007/0054867 for preparation of for instance {4-[(5-bromo-2-chloro-phenyl)-methyl]-phenoxy}-tert-butyl-dimethyl-silane).

In step 2 of Scheme 5, when Pg$^2$=PMB, intermediate (V-i) is treated with an acid like trifluoroacetic acid, methanesulfonic acid or an acidic resin in presence of anisole in a solvent like dichloromethane at a temperature ranging from about −10 degrees Celsius to about room temperature to produce intermediate (V-j).

In step 3 of Scheme 5, protecting groups (Pg$^5$) and (Pg$^1$) can be removed to provide (V-k). Typically (Pg$_5$) is TBS and Pg' is Bn. In this circumstance, the protecting groups are removed by sequential treatment of (V-j) with 1) tetrabutylammonium fluoride in a solvent like tetrahydrofuran or 2-methyltetrahydrofuran at a temperature ranging from 0 degrees Celsius to about 40 degrees Celsius and 2) treatment with formic acid in the presence of palladium (Pd black) in a protic solvent (e.g., ethanol/THF) at about room temperature. In this sequence, the order of the 2 reactions is interchangeable.

In step 4 of Scheme 5, intermediate (V-k) is treated with N,N-bis-(trifluoromethanesulfonyl)-aniline in presence of a base like triethylamine or 4-dimethyaminopyridine in a solvent like dichloromethane or 1,2-dichloroethane at a temperature ranging from 0 degrees Celsius to about 40 degrees Celsius to produce intermediate (V-1).

In step 5 of Scheme 5, intermediate (V-1) is subjected to a Sonogashira-type reaction (see, Sonogashira, K. Coupling Reactions Between sp$^2$ and sp Carbon Centers. In *Comprehensive Organic Synthesis* (eds. Trost, B. M., Fleming, I.), 3, 521-549, (Pergamon, Oxford, 1991)). For instance (V-1) is treated with the appropriate terminal alkyne HCCR$^6$ in presence of copper(I) iodide, a catalyst like bis-(triphenylphosphine)-palladium dichloride or tetrakis(triphenylphosphine)palladium(0) in presence of a base like triethylamine or N,N-diisopropylethylamine in a solvent like N,N-dimethylformamide at a temperature ranging from about room temperature to about 120 degrees Celsius to produce the desired product (A) and (B). When R$^6$ is H, it is more convenient to use trimethylsilylacetylene. In this case the crude material obtained from the reaction described above is treated with a base like potassium carbonate in an alcoholic solvent like MeOH at about room temperature to produce the desired product (A) and (B) where R$^2$ is —CCH after classical work-up known by those skilled in the art.

One skilled in the art would understand that the chemistry described above in schemes 1 to 5, represents different ways of accessing intermediate (V-k). In turn, particularly when R$^1$ is Cl, (V-k) can be treated with an alkylating agent of choice under classical conditions to selectively alkylate the phenol group to produce (A) (and (B) in schemes 1 and 5) where R$^2$ is (C$_1$-C$_4$)alkoxy.

The compounds of the present invention contain asymmetric or chiral centers, and, therefore, exist in different stereoisomeric forms. Unless a specific enationmer or diastereomer is indicated, the invention includes all possible enantiomers and diastereomers and mixtures of two or more stereoisomers, for example mixtures of enantiomers and/or diastereomers, in all ratios.

Diastereomeric mixtures can be separated into their individual diastereoisomers on the basis of their physical chemical differences by methods well known to those skilled in the art, such as by chromatography and/or fractional crystallization, distillation and sublimation. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered of use of this invention. Enantiomers can also be separated by use of a chiral HPLC (high pressure liquid chromatography) column.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons. The equilibrium between closed and opened form of some intermediates (and/or mixtures of intermediates) is reminiscent of the process of mutarotation involving aldoses, known by those skilled in the art.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with alternative isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate occupancy. Isotopically labeled compounds of the present invention can generally be prepared by following procedures analogous to those disclosed in the Schemes and/or in the description herein, by substituting an isotopically labeled reagent for a non-isotopically labeled reagent.

In certain embodiments, the compounds described herein are used in the methods of the present invention for treating, preventing or reducing the risk of cardiovascular diseases, conditions and/or disorders modulated by the inhibition of the sodium-glucose transporters (in particular SGLT-2) in animals with pre-diabetes.

Humans with pre-diabetes are individuals that have an A1C level between 5.7%-6.4%. An A1C test typically measures your average blood glucose over a period of 2 to 3 months. Pre-diabetes can also be measured using a fasting glucose test (FGT). Humans with pre-diabetes are individuals that have a fasting plasma glucose level between 100 mg/dl to 125 mg/dl. Alternatively, pre-diabetes can also be measured using an oral glucose tolerance test (OGTT). Humans with pre-diabetes are individuals that have a glucose level between 140 mg/dl to 199 mg/dl after 2 hours from the administered the OGTT.

In certain embodiments, the compounds described herein are used in the methods of the present invention for treating, preventing or reducing the risk of cardiovascular diseases, conditions and/or disorders modulated by the inhibition of the sodium-glucose transporters (in particular SGLT-2) in animals with type 1 or type 2 diabetes.

Humans with diabetes are individuals that have an A1C level of 6.5% or higher. Humans with diabetes are individuals that have a fasting plasma glucose level of 126 mg/dl or higher. Humans with diabetes are individuals that have a glucose level of 200 mg/dl or higher after being administered the OGTT.

In certain embodiments, the compounds described herein are used in the methods of the present invention for treating, preventing or reducing the risk of cardiovascular diseases, conditions and/or disorders modulated by the inhibition of the sodium-glucose transporters (in particular SGLT-2) in animals without pre-diabetes or type 1 or type 2 diabetes. Humans without pre-diabetes or type 1 or type 2 diabetes, are individuals that have an A1C level of 5.6% or lower. Humans without pre-diabetes or type 1 or type 2 diabetes, are individuals that have a fasting plasma glucose level of 99 mg/dl or lower. Humans without pre-diabetes or type 1 or type 2 diabetes, are individuals that have a glucose level of 139 mg/dl or lower after being administered the OGTT.

In one embodiment of the methods described herein, the method comprises treating heart failure in an animal comprising administering ertugliflozin or a pharmaceutically acceptable salt or a co-crystal thereof, to an animal with pre-diabetes. In another embodiment of the methods described herein, the method comprises preventing heart failure in an animal comprising administering ertugliflozin or a pharmaceutically acceptable salt or a co-crystal thereof, to an animal with pre-diabetes. In another embodiment of the methods described herein, the method comprises reducing the risk of heart failure in an animal comprising administering ertugliflozin or a pharmaceutically acceptable salt or a co-crystal thereof, to an animal with pre-diabetes.

In one embodiment of the methods described herein, the method comprises treating myocardial infarction in an animal comprising administering ertugliflozin or a pharmaceutically acceptable salt or a co-crystal thereof, to an animal with pre-diabetes. In another embodiment of the methods described herein, the method comprises preventing myocardial infarction in an animal comprising administering ertugliflozin or a pharmaceutically acceptable salt or a co-crystal thereof, to an animal with pre-diabetes. In another embodiment of the methods described herein, the method comprises reducing the risk of myocardial infarction in an animal comprising administering ertugliflozin or a pharmaceutically acceptable salt or a co-crystal thereof, to an animal with pre-diabetes.

In one embodiment of the methods described herein, the method comprises treating cardiovascular disease in an animal comprising administering ertugliflozin or a pharmaceutically acceptable salt or a co-crystal thereof, to an animal with pre-diabetes. In another embodiment of the methods described herein, the method comprises preventing cardiovascular disease in an animal comprising administering ertugliflozin or a pharmaceutically acceptable salt or a co-crystal thereof, to an animal with pre-diabetes. In another embodiment of the methods described herein, the method comprises reducing the risk of cardiovascular disease in an animal comprising administering ertugliflozin or a pharmaceutically acceptable salt or a co-crystal thereof, to an animal with pre-diabetes.

In one embodiment of the methods described herein, the method comprises preventing cardiovascular death in an animal comprising administering ertugliflozin or a pharmaceutically acceptable salt or a co-crystal thereof, to an animal with pre-diabetes. In another embodiment of the methods described herein, the method comprises reducing the risk of cardiovascular death in an animal comprising administering ertugliflozin or a pharmaceutically acceptable salt or a co-crystal thereof, to an animal with pre-diabetes.

In one embodiment of the methods described herein, the method comprises treating heart failure in an animal comprising administering ertugliflozin or a pharmaceutically acceptable salt or a co-crystal thereof, to an animal with type 1 or type 2 diabetes. In another embodiment of the methods described herein, the method comprises preventing heart failure in an animal comprising administering ertugliflozin or a pharmaceutically acceptable salt or a co-crystal thereof, to an animal with 1 or type 2 diabetes. In another embodiment of the methods described herein, the method comprises reducing the risk of heart failure in an animal comprising administering ertugliflozin or a pharmaceutically acceptable salt or a co-crystal thereof, to an animal with 1 or type 2 diabetes.

In one embodiment of the methods described herein, the method comprises treating myocardial infarction in an animal comprising administering ertugliflozin or a pharmaceutically acceptable salt or a co-crystal thereof, to an animal with 1 or type 2 diabetes. In another embodiment of the methods described herein, the method comprises preventing myocardial infarction in an animal comprising administering ertugliflozin or a pharmaceutically acceptable salt or a co-crystal thereof, to an animal with 1 or type 2 diabetes. In another embodiment of the methods described herein, the method comprises reducing the risk of myocardial infarction in an animal comprising administering ertugliflozin or a pharmaceutically acceptable salt or a co-crystal thereof, to an animal with 1 or type 2 diabetes.

In one embodiment of the methods described herein, the method comprises treating cardiovascular disease in an animal comprising administering ertugliflozin or a pharmaceutically acceptable salt or a co-crystal thereof, to an animal with 1 or type 2 diabetes. In another embodiment of the methods described herein, the method comprises preventing cardiovascular disease in an animal comprising administering ertugliflozin or a pharmaceutically acceptable salt or a co-crystal thereof, to an animal with 1 or type 2 diabetes. In another embodiment of the methods described herein, the method comprises reducing the risk of cardiovascular disease in an animal comprising administering ertugliflozin or a pharmaceutically acceptable salt or a co-crystal thereof, to an animal with 1 or type 2 diabetes.

In one embodiment of the methods described herein, the method comprises preventing cardiovascular death in an animal comprising administering ertugliflozin or a pharmaceutically acceptable salt or a co-crystal thereof, to an animal with 1 or type 2 diabetes. In another embodiment of the methods described herein, the method comprises reducing the risk of cardiovascular death in an animal comprising administering ertugliflozin or a pharmaceutically acceptable salt or a co-crystal thereof, to an animal with 1 or type 2 diabetes.

In one embodiment of the methods described herein, the method comprises treating heart failure in an animal comprising administering ertugliflozin or a pharmaceutically acceptable salt or a co-crystal thereof, to an animal without pre-diabetes, type 1 or type 2 diabetes. In another embodiment of the methods described herein, the method comprises preventing heart failure in an animal comprising administering ertugliflozin or a pharmaceutically acceptable salt or a co-crystal thereof, to an animal without pre-diabetes, type 1 or type 2 diabetes. In another embodiment of the methods described herein, the method comprises reducing the risk of heart failure in an animal comprising administering ertugliflozin or a pharmaceutically acceptable salt or a co-crystal thereof, to an animal without pre-diabetes, type 1 or type 2 diabetes.

In one embodiment of the methods described herein, the method comprises treating myocardial infarction in an animal comprising administering ertugliflozin or a pharmaceutically acceptable salt or a co-crystal thereof, to an animal without pre-diabetes, type 1 or type 2 diabetes. In another embodiment of the methods described herein, the method comprises preventing myocardial infarction in an animal comprising administering ertugliflozin or a pharmaceutically acceptable salt or a co-crystal thereof, to an animal without pre-diabetes, type 1 or type 2 diabetes. In another embodiment of the methods described herein, the method comprises reducing the risk of myocardial infarction in an animal comprising administering ertugliflozin or a pharmaceutically acceptable salt or a co-crystal thereof, to an animal without pre-diabetes, type 1 or type 2 diabetes.

In one embodiment of the methods described herein, the method comprises treating cardiovascular disease in an animal comprising administering ertugliflozin or a pharmaceutically acceptable salt or a co-crystal thereof, to an animal without pre-diabetes, type 1 or type 2 diabetes. In another embodiment of the methods described herein, the method comprises preventing cardiovascular disease in an animal comprising administering ertugliflozin or a pharmaceutically acceptable salt or a co-crystal thereof, to an animal without pre-diabetes, type 1 or type 2 diabetes. In another embodiment of the methods described herein, the method comprises reducing the risk of cardiovascular disease in an animal comprising administering ertugliflozin or a pharmaceutically acceptable salt or a co-crystal thereof, to an animal without pre-diabetes, type 1 or type 2 diabetes.

In one embodiment of the methods described herein, the method comprises preventing cardiovascular death in an animal comprising administering ertugliflozin or a pharmaceutically acceptable salt or a co-crystal thereof, to an animal without pre-diabetes, type 1 or type 2 diabetes. In another embodiment of the methods described herein, the method comprises reducing the risk of cardiovascular death in an animal comprising administering ertugliflozin or a pharmaceutically acceptable salt or a co-crystal thereof, to an animal without pre-diabetes, type 1 or type 2 diabetes.

In one embodiment of the methods described herein, the method comprises treating heart failure in an animal comprising administering ertugliflozin or a pharmaceutically acceptable salt or a co-crystal thereof, in combination with sitagliptin, or a pharmaceutically acceptable salt thereof, to an animal with pre-diabetes. In another embodiment of the methods described herein, the method comprises preventing heart failure in an animal comprising administering ertugliflozin or a pharmaceutically acceptable salt or a co-crystal thereof, in combination with sitagliptin, or a pharmaceutically acceptable salt thereof, to an animal with pre-diabetes. In another embodiment of the methods described herein, the method comprises reducing the risk of heart failure in an animal comprising administering ertugliflozin or a pharmaceutically acceptable salt or a co-crystal thereof, in combination with sitagliptin, or a pharmaceutically acceptable salt thereof, to an animal with pre-diabetes.

In one embodiment of the methods described herein, the method comprises treating myocardial infarction in an animal comprising administering ertugliflozin or a pharmaceutically acceptable salt or a co-crystal thereof, in combination with sitagliptin, or a pharmaceutically acceptable salt thereof, to an animal with pre-diabetes. In another embodiment of the methods described herein, the method comprises preventing myocardial infarction in an animal comprising administering ertugliflozin or a pharmaceutically acceptable salt or a co-crystal thereof, in combination with sitagliptin, or a pharmaceutically acceptable salt thereof, to an animal with pre-diabetes. In another embodiment of the methods described herein, the method comprises reducing the risk of myocardial infarction in an animal comprising administering ertugliflozin or a pharmaceutically acceptable salt or a co-crystal thereof, in combination with sitagliptin, or a pharmaceutically acceptable salt thereof, to an animal with pre-diabetes.

In one embodiment of the methods described herein, the method comprises treating cardiovascular disease in an animal comprising administering ertugliflozin or a pharmaceutically acceptable salt or a co-crystal thereof, in combination with sitagliptin, or a pharmaceutically acceptable salt thereof, to an animal with pre-diabetes. In another embodiment of the methods described herein, the method comprises preventing cardiovascular disease in an animal comprising administering ertugliflozin or a pharmaceutically acceptable salt or a co-crystal thereof, in combination with sitagliptin, or a pharmaceutically acceptable salt thereof, to an animal with pre-diabetes. In another embodiment of the methods described herein, the method comprises reducing the risk of cardiovascular disease in an animal comprising administering ertugliflozin or a pharmaceutically acceptable salt or a co-crystal thereof, in combination with sitagliptin, or a pharmaceutically acceptable salt thereof, to an animal with pre-diabetes.

In one embodiment of the methods described herein, the method comprises preventing cardiovascular death in an animal comprising administering ertugliflozin or a pharmaceutically acceptable salt or a co-crystal thereof, in combination with sitagliptin, or a pharmaceutically acceptable salt thereof, to an animal with pre-diabetes. In another embodiment of the methods described herein, the method comprises reducing the risk of cardiovascular death in an animal comprising administering ertugliflozin or a pharmaceutically acceptable salt or a co-crystal thereof, in combination with sitagliptin, or a pharmaceutically acceptable salt thereof, to an animal with pre-diabetes.

In one embodiment of the methods described herein, the method comprises treating heart failure in an animal comprising administering ertugliflozin or a pharmaceutically acceptable salt or a co-crystal thereof, in combination with sitagliptin, or a pharmaceutically acceptable salt thereof, to an animal with type 1 or type 2 diabetes. In another embodiment of the methods described herein, the method comprises preventing heart failure in an animal comprising administering ertugliflozin or a pharmaceutically acceptable salt or a co-crystal thereof, in combination with sitagliptin, or a pharmaceutically acceptable salt thereof, to an animal with 1 or type 2 diabetes. In another embodiment of the methods described herein, the method comprises reducing the risk of heart failure in an animal comprising administering ertugliflozin or a pharmaceutically acceptable salt or a co-crystal thereof, in combination with sitagliptin, or a pharmaceutically acceptable salt thereof, to an animal with 1 or type 2 diabetes. In one embodiment of the methods described herein, the method comprises treating myocardial infarction in an animal comprising administering ertugliflozin or a pharmaceutically acceptable salt or a co-crystal thereof, in combination with sitagliptin, or a pharmaceutically acceptable salt thereof, to an animal with 1 or type 2 diabetes. In another embodiment of the methods described herein, the method comprises preventing myocardial infarction in an animal comprising administering ertugliflozin or a pharmaceutically acceptable salt or a co-crystal thereof, in combination with sitagliptin, or a pharmaceutically acceptable salt thereof, to an animal with 1 or type 2 diabetes. In another embodiment of the methods described herein, the method comprises reducing the risk of myocardial infarction in an animal comprising administering ertugliflozin or a pharmaceutically acceptable salt or a co-crystal thereof, in combination with sitagliptin, or a pharmaceutically acceptable salt thereof, to an animal with 1 or type 2 diabetes.

In one embodiment of the methods described herein, the method comprises treating cardiovascular disease in an animal comprising administering ertugliflozin or a pharmaceutically acceptable salt or a co-crystal thereof, in combination with sitagliptin, or a pharmaceutically acceptable salt thereof, to an animal with 1 or type 2 diabetes. In another embodiment of the methods described herein, the method comprises preventing cardiovascular disease in an animal comprising administering ertugliflozin or a pharmaceutically acceptable salt or a co-crystal thereof, in combination with sitagliptin, or a pharmaceutically acceptable salt thereof, to an animal with 1 or type 2 diabetes. In another embodiment of the methods described herein, the method comprises in an animal reducing the risk of cardiovascular disease comprising administering ertugliflozin or a pharmaceutically acceptable salt or a co-crystal thereof, in combination with sitagliptin, or a pharmaceutically acceptable salt thereof, to an animal with 1 or type 2 diabetes.

In one embodiment of the methods described herein, the method comprises preventing cardiovascular death in an animal comprising administering ertugliflozin or a pharmaceutically acceptable salt or a co-crystal thereof, in combination with sitagliptin, or a pharmaceutically acceptable salt thereof, to an animal with 1 or type 2 diabetes. In another embodiment of the methods described herein, the method comprises reducing the risk of cardiovascular death in an animal comprising administering ertugliflozin or a pharmaceutically acceptable salt or a co-crystal thereof, in combination with sitagliptin, or a pharmaceutically acceptable salt thereof, to an animal with 1 or type 2 diabetes.

In one embodiment of the methods described herein, the method comprises treating heart failure in an animal comprising administering ertugliflozin or a pharmaceutically acceptable salt or a co-crystal thereof, in combination with sitagliptin, or a pharmaceutically acceptable salt thereof, to an animal without pre-diabetes, type 1 or type 2 diabetes. In another embodiment of the methods described herein, the method comprises preventing heart failure in an animal comprising administering ertugliflozin or a pharmaceutically acceptable salt or a co-crystal thereof, in combination with sitagliptin, or a pharmaceutically acceptable salt thereof, to an animal without pre-diabetes, type 1 or type 2 diabetes. In another embodiment of the methods described herein, the method comprises reducing the risk of heart failure in an animal comprising administering ertugliflozin or a pharmaceutically acceptable salt or a co-crystal thereof, in combination with sitagliptin, or a pharmaceutically acceptable salt thereof, to an animal without pre-diabetes, type 1 or type 2 diabetes.

In one embodiment of the methods described herein, the method comprises treating myocardial infarction in an animal comprising administering ertugliflozin or a pharmaceutically acceptable salt or a co-crystal thereof, in combination with sitagliptin, or a pharmaceutically acceptable salt thereof, to an animal without pre-diabetes, type 1 or type 2 diabetes. In another embodiment of the methods described herein, the method comprises preventing myocardial infarction in an animal comprising administering ertugliflozin or a pharmaceutically acceptable salt or a co-crystal thereof, in combination with sitagliptin, or a pharmaceutically acceptable salt thereof, to an animal without pre-diabetes, type 1 or type 2 diabetes. In another embodiment of the methods described herein, the method comprises reducing the risk of myocardial infarction in an animal comprising administering ertugliflozin or a pharmaceutically acceptable salt or a co-crystal thereof, in combination with sitagliptin, or a pharmaceutically acceptable salt thereof, to an animal without pre-diabetes, type 1 or type 2 diabetes.

In one embodiment of the methods described herein, the method comprises treating cardiovascular disease in an animal comprising administering ertugliflozin or a pharmaceutically acceptable salt or a co-crystal thereof, in combination with sitagliptin, or a pharmaceutically acceptable salt thereof, to an animal without pre-diabetes, type 1 or type 2 diabetes. In another embodiment of the methods described herein, the method comprises preventing cardiovascular disease in an animal comprising administering ertugliflozin or a pharmaceutically acceptable salt or a co-crystal thereof, in combination with sitagliptin, or a pharmaceutically acceptable salt thereof, to an animal without pre-diabetes, type 1 or type 2 diabetes. In another embodiment of the methods described herein, the method comprises reducing the risk of cardiovascular disease in an animal comprising administering ertugliflozin or a pharmaceutically acceptable salt or a co-crystal thereof, in combination with sitagliptin, or a pharmaceutically acceptable salt thereof, to an animal without pre-diabetes, type 1 or type 2 diabetes.

In one embodiment of the methods described herein, the method comprises preventing cardiovascular death in an animal comprising administering ertugliflozin or a pharmaceutically acceptable salt or a co-crystal thereof, in combination with sitagliptin, or a pharmaceutically acceptable salt thereof, to an animal without pre-diabetes, type 1 or type 2 diabetes. In another embodiment of the methods described herein, the method comprises reducing the risk of cardiovascular death in an animal comprising administering ertugliflozin or a pharmaceutically acceptable salt or a co-crystal thereof, in combination with sitagliptin, or a pharmaceutically acceptable salt thereof, to an animal without pre-diabetes, type 1 or type 2 diabetes.

In one embodiment of the methods described herein, the method comprises treating heart failure in an animal comprising administering ertugliflozin or a pharmaceutically acceptable salt or a co-crystal thereof, in combination with metformin, or a pharmaceutically acceptable salt thereof, to an animal with pre-diabetes. In another embodiment of the methods described herein, the method comprises preventing heart failure in an animal comprising administering ertugliflozin or a pharmaceutically acceptable salt or a co-crystal thereof, in combination with metformin, or a pharmaceutically acceptable salt thereof, to an animal with pre-diabetes. In another embodiment of the methods described herein, the method comprises reducing the risk of heart failure in an animal comprising administering ertugliflozin or a pharmaceutically acceptable salt or a co-crystal thereof, in combination with metformin, or a pharmaceutically acceptable salt thereof, to an animal with pre-diabetes.

In one embodiment of the methods described herein, the method comprises treating myocardial infarction in an animal comprising administering ertugliflozin or a pharmaceutically acceptable salt or a co-crystal thereof, in combination with metformin, or a pharmaceutically acceptable salt thereof, to an animal with pre-diabetes. In another embodiment of the methods described herein, the method comprises preventing myocardial infarction in an animal comprising administering ertugliflozin or a pharmaceutically acceptable salt or a co-crystal thereof, in combination with metformin, or a pharmaceutically acceptable salt thereof, to an animal with pre-diabetes. In another embodiment of the methods described herein, the method comprises reducing the risk of myocardial infarction in an animal comprising administering ertugliflozin or a pharmaceutically acceptable salt or a co-crystal thereof, in combination with metformin, or a pharmaceutically acceptable salt thereof, to an animal with pre-diabetes.

In one embodiment of the methods described herein, the method comprises treating cardiovascular disease in an animal comprising administering ertugliflozin or a pharmaceutically acceptable salt or a co-crystal thereof, in combination with metformin, or a pharmaceutically acceptable salt thereof, to an animal with pre-diabetes. In another embodiment of the methods described herein, the method comprises preventing cardiovascular disease in an animal comprising administering ertugliflozin or a pharmaceutically acceptable salt or a co-crystal thereof, in combination with metformin, or a pharmaceutically acceptable salt thereof, to an animal with pre-diabetes. In another embodiment of the methods described herein, the method comprises reducing the risk of cardiovascular disease in an animal comprising administering ertugliflozin or a pharmaceutically acceptable salt or a co-crystal thereof, in combination with metformin, or a pharmaceutically acceptable salt thereof, to an animal with pre-diabetes.

In one embodiment of the methods described herein, the method comprises preventing cardiovascular death in an animal comprising administering ertugliflozin or a pharmaceutically acceptable salt or a co-crystal thereof, in combination with metformin, or a pharmaceutically acceptable salt thereof, to an animal with pre-diabetes. In another embodiment of the methods described herein, the method comprises reducing the risk of cardiovascular death in an animal comprising administering ertugliflozin or a pharmaceutically acceptable salt or a co-crystal thereof, in combination with metformin, or a pharmaceutically acceptable salt thereof, to an animal with pre-diabetes.

In one embodiment of the methods described herein, the method comprises treating heart failure in an animal comprising administering ertugliflozin or a pharmaceutically acceptable salt or a co-crystal thereof, in combination with metformin, or a pharmaceutically acceptable salt thereof, to an animal with type 1 or type 2 diabetes. In another embodiment of the methods described herein, the method comprises preventing heart failure in an animal comprising administering ertugliflozin or a pharmaceutically acceptable salt or a co-crystal thereof, in combination with metformin, or a pharmaceutically acceptable salt thereof, to an animal with 1 or type 2 diabetes. In another embodiment of the methods described herein, the method comprises reducing the risk of heart failure in an animal comprising administering ertugliflozin or a pharmaceutically acceptable salt or a co-crystal thereof, in combination with metformin, or a pharmaceutically acceptable salt thereof, to an animal with 1 or type 2 diabetes.

In one embodiment of the methods described herein, the method comprises treating myocardial infarction in an animal comprising administering ertugliflozin or a pharmaceutically acceptable salt or a co-crystal thereof, in combination with metformin, or a pharmaceutically acceptable salt thereof, to an animal with 1 or type 2 diabetes. In another embodiment of the methods described herein, the method comprises preventing myocardial infarction in an animal comprising administering ertugliflozin or a pharmaceutically acceptable salt or a co-crystal thereof, in combination with metformin, or a pharmaceutically acceptable salt thereof, to an animal with 1 or type 2 diabetes. In another embodiment of the methods described herein, the method comprises reducing the risk of myocardial infarction in an animal comprising administering ertugliflozin or a pharmaceutically acceptable salt or a co-crystal thereof, in combination with metformin, or a pharmaceutically acceptable salt thereof, to an animal with 1 or type 2 diabetes.

In one embodiment of the methods described herein, the method comprises treating cardiovascular disease in an animal comprising administering ertugliflozin or a pharmaceutically acceptable salt or a co-crystal thereof, in combination with metformin, or a pharmaceutically acceptable salt thereof, to an animal with 1 or type 2 diabetes. In another embodiment of the methods described herein, the method comprises preventing cardiovascular disease in an animal comprising administering ertugliflozin or a pharmaceutically acceptable salt or a co-crystal thereof, in combination with metformin, or a pharmaceutically acceptable salt thereof, to an animal with 1 or type 2 diabetes. In another embodiment of the methods described herein, the method comprises reducing the risk of cardiovascular disease in an animal comprising administering ertugliflozin or a pharmaceutically acceptable salt or a co-crystal thereof, in combination with metformin, or a pharmaceutically acceptable salt thereof, to an animal with 1 or type 2 diabetes.

In one embodiment of the methods described herein, the method comprises preventing cardiovascular death in an animal comprising administering ertugliflozin or a pharmaceutically acceptable salt or a co-crystal thereof, in combination with metformin, or a pharmaceutically acceptable salt thereof, to an animal with 1 or type 2 diabetes. In another embodiment of the methods described herein, the method comprises reducing the risk of cardiovascular death in an animal comprising administering ertugliflozin or a pharmaceutically acceptable salt or a co-crystal thereof, in combination with metformin, or a pharmaceutically acceptable salt thereof, to an animal with 1 or type 2 diabetes.

In one embodiment of the methods described herein, the method comprises treating heart failure in an animal comprising administering ertugliflozin or a pharmaceutically acceptable salt or a co-crystal thereof, in combination with metformin, or a pharmaceutically acceptable salt thereof, to an animal without pre-diabetes, type 1 or type 2 diabetes. In another embodiment of the methods described herein, the method comprises preventing heart failure in an animal comprising administering ertugliflozin or a pharmaceutically acceptable salt or a co-crystal thereof, in combination with metformin, or a pharmaceutically acceptable salt thereof, to an animal without pre-diabetes, type 1 or type 2 diabetes. In another embodiment of the methods described herein, the method comprises reducing the risk of heart failure in an animal comprising administering ertugliflozin or a pharmaceutically acceptable salt or a co-crystal thereof, in combination with metformin, or a pharmaceutically acceptable salt thereof, to an animal without pre-diabetes, type 1 or type 2 diabetes.

In one embodiment of the methods described herein, the method comprises treating myocardial infarction in an animal comprising administering ertugliflozin or a pharmaceutically acceptable salt or a co-crystal thereof, in combination with metformin, or a pharmaceutically acceptable salt thereof, to an animal without pre-diabetes, type 1 or type 2 diabetes. In another embodiment of the methods described herein, the method comprises preventing myocardial infarction in an animal comprising administering ertugliflozin or a pharmaceutically acceptable salt or a co-crystal thereof, in combination with metformin, or a pharmaceutically acceptable salt thereof, to an animal without pre-diabetes, type 1 or type 2 diabetes. In another embodiment of the methods described herein, the method comprises reducing the risk of myocardial infarction in an animal comprising administering ertugliflozin or a pharmaceutically acceptable salt or a co-crystal thereof, in combination with metformin, or a pharmaceutically acceptable salt thereof, to an animal without pre-diabetes, type 1 or type 2 diabetes.

In one embodiment of the methods described herein, the method comprises treating cardiovascular disease in an animal comprising administering ertugliflozin or a pharmaceutically acceptable salt or a co-crystal thereof, in combination with metformin, or a pharmaceutically acceptable salt thereof, to an animal without pre-diabetes, type 1 or type 2 diabetes. In another embodiment of the methods described herein, the method comprises preventing cardiovascular disease in an animal comprising administering ertugliflozin or a pharmaceutically acceptable salt or a co-crystal thereof, in combination with metformin, or a pharmaceutically acceptable salt thereof, to an animal without pre-diabetes, type 1 or type 2 diabetes. In another embodiment of the methods described herein, the method comprises reducing the risk of cardiovascular disease in an animal comprising administering ertugliflozin or a pharmaceutically acceptable salt or a co-crystal thereof, in combination with metformin, or a pharmaceutically acceptable salt thereof, to an animal without pre-diabetes, type 1 or type 2 diabetes.

In one embodiment of the methods described herein, the method comprises preventing cardiovascular death in an animal comprising administering ertugliflozin or a pharmaceutically acceptable salt or a co-crystal thereof, in combination with metformin, or a pharmaceutically acceptable salt thereof, to an animal without pre-diabetes, type 1 or type 2 diabetes. In another embodiment of the methods described herein, the method comprises reducing the risk of cardiovascular death in an animal comprising administering ertugliflozin or a pharmaceutically acceptable salt or a co-crystal thereof, in combination with metformin, or a pharmaceutically acceptable salt thereof, to an animal without pre-diabetes, type 1 or type 2 diabetes.

In one aspect, in any one of the methods of use described above, ertugliflozin or a pharmaceutically acceptable salt or a co-crystal thereof is administered once daily to an animal, i.e. for example 5 mg or 15 mg of ertugliflozin or a pharmaceutically acceptable salt or a co-crystal thereof is administered once daily to an animal, preferably human.

In another aspect, in any one of the methods of use described above, ertugliflozin or a pharmaceutically acceptable salt or a co-crystal thereof is administered more than once daily to an animal, i.e. for example 2.5 mg or 7.5 mg of ertugliflozin or a pharmaceutically acceptable salt or a co-crystal thereof is administered twice daily to an animal, preferably human.

Another embodiment of the present invention is a pharmaceutical composition for use in the methods described herein comprising a therapeutically effective amount of a compound described herein and a pharmaceutically acceptable excipient, diluent or carrier. The compounds described herein (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the animal an elegant and easily handleable product.

Tables 1, 2 and 3 show examples of pharmaceutical formulations in accordance with the embodiments of the present invention:

TABLE 1

| Component | Amount (%) |
|---|---|
| Ertugliflozin | 0.5-15 |
| Microcrystalline Cellulose | 10-50 |
| Dibasic calcium phosphate anhydrous | 10-50 |
| Croscarmellose Sodium | 0.5-5 |
| Sodium Stearyl Fumarate | 0.5-5 |
| Magnesium Stearate | 0.5-2 |
| Opadry 20A | 1-6 |
| Carnauba Wax | 0.001-0.005 |

TABLE 2

| Component | Amount (%) |
|---|---|
| Sitagliptin | 10-50 |
| Ertugliflozin | 0.5-15 |

TABLE 2-continued

| Component | Amount (%) |
|---|---|
| Microcrystalline Cellulose | 10-50 |
| Dibasic calcium phosphate anhydrous | 10-50 |
| Croscarmellose Sodium | 0.5-5 |
| Sodium Stearyl Fumarate | 0.5-5 |
| Magnesium Stearate | 0.5-2 |
| Opadry 20A | 1-6 |
| Carnauba Wax | 0.001-0.005 |

TABLE 3

| Component | Amount (%) |
|---|---|
| Metformin, or a pharmaceutically acceptable salt thereof | 10-50 |
| Ertugliflozin | 0.5-15 |
| Microcrystalline Cellulose | 10-50 |
| Dibasic calcium phosphate anhydrous | 10-50 |
| Croscarmellose Sodium | 0.5-5 |
| Sodium Stearyl Fumarate | 0.5-5 |
| Magnesium Stearate | 0.5-2 |
| Opadry 20A | 1-6 |
| Carnauba Wax | 0.001-0.005 |

The pharmaceutical compositions also include solvates and hydrates of the compounds of Formula (A) or Formula (B). The term "solvate" refers to a molecular complex of a compound represented by Formula (A) or Formula (B) (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecuR$^1$ is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. The crystalline forms may also exist as complexes with other innocuous small molecules, such as L-phenylalanine, L-proline, L-pyroglutamic acid and the like, as co-crystals or solvates or hydrates of the co-crystalline material. The solvates, hydrates and co-crystalline compounds may be prepared using procedures described in PCT Publication No. WO 08/002824, incorporated herein by reference, or other procedures well-known to those of skill in the art.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent inadvertent access to the contents of the package. In addition, the container has deposited thereon a label that describes the contents of the container. The label may also include appropriate warnings.

In certain embodiments of the methods described herein, ertugliflozin or a pharmaceutically acceptable salt or a co-crystal thereof is administered in combination with sitagliptin and/or metformin, or a pharmaceutically acceptable salt thereof.

Ertugliflozin or a pharmaceutically acceptable salt or a co-crystal thereof can, for example, be administered in the amount of 2.5 mg while sitagliptin can be administered in the amount of 25 mg. Ertugliflozin or a pharmaceutically acceptable salt or a co-crystal thereof can be administered in the amount of 2.5 mg while sitagliptin can be administered in the amount of 50 mg. Ertugliflozin or a pharmaceutically acceptable salt or a co-crystal thereof can be administered in the amount of 2.5 mg while sitagliptin can be administered in the amount of 100 mg.

Ertugliflozin or a pharmaceutically acceptable salt or a co-crystal thereof can be administered in the amount of 5 mg while sitagliptin can be administered in the amount of 25 mg. Ertugliflozin or a pharmaceutically acceptable salt or a co-crystal thereof can be administered in the amount of 5 mg while sitagliptin can be administered in the amount of 50 mg. Ertugliflozin or a pharmaceutically acceptable salt or a co-crystal thereof can be administered in the amount of 5 mg while sitagliptin can be administered in the amount of 100 mg.

Ertugliflozin or a pharmaceutically acceptable salt or a co-crystal thereof can be administered in the amount of 7.5 mg while sitagliptin can be administered in the amount of 25 mg. Ertugliflozin or a pharmaceutically acceptable salt or a co-crystal thereof can be administered in the amount of 7.5 mg while sitagliptin can be administered in the amount of 50 mg. Ertugliflozin or a pharmaceutically acceptable salt or a co-crystal thereof can be administered in the amount of 7.5 mg while sitagliptin can be administered in the amount of 100 mg.

Ertugliflozin or a pharmaceutically acceptable salt or a co-crystal thereof can be administered in the amount of 15 mg while sitagliptin can be administered in the amount of 25 mg. Ertugliflozin or a pharmaceutically acceptable salt or a co-crystal thereof can be administered in the amount of 15 mg while sitagliptin can be administered in the amount of 50 mg. Ertugliflozin or a pharmaceutically acceptable salt or a co-crystal thereof can be administered in the amount of 15 mg while sitagliptin can be administered in the amount of 100 mg.

Such combinations (ertugliflozin and sitagliptin) can be administered simultaneously or sequentially. Such combinations can be in a single pharmaceutical compositions or each pharmaceutical agent can be in a separate pharmaceutical composition. Such combinations can be can be administered once, twice or three times daily.

If administered with metformin, or a pharmaceutically acceptable salt thereof, metformin, or a pharmaceutically acceptable salt thereof can be administered, for example, in the amount of 500 mg, 850 mg, 1000 mg, 1700 mg or 2000 mg. Ertugliflozin or a pharmaceutically acceptable salt or a co-crystal thereof can be administered in the amount of 2.5 mg while metformin, or a pharmaceutically acceptable salt thereof can be administered in the amount of 500 mg. Ertugliflozin or a pharmaceutically acceptable salt or a co-crystal thereof can be administered in the amount of 2.5 mg while metformin, or a pharmaceutically acceptable salt thereof can be administered in the amount of 850 mg. Ertugliflozin or a pharmaceutically acceptable salt or a co-crystal thereof can be administered in the amount of 2.5 mg while metformin, or a pharmaceutically acceptable salt thereof can be administered in the amount of 1000 mg. Ertugliflozin or a pharmaceutically acceptable salt or a co-crystal thereof can be administered in the amount of 2.5 mg while metformin, or a pharmaceutically acceptable salt thereof can be administered in the amount of 1700 mg. Ertugliflozin or a pharmaceutically acceptable salt or a co-crystal thereof can be administered in the amount of 2.5 mg while metformin, or a pharmaceutically acceptable salt thereof can be administered in the amount of 2000 mg.

Ertugliflozin or a pharmaceutically acceptable salt or a co-crystal thereof can be administered in the amount of 5 mg while metformin, or a pharmaceutically acceptable salt thereof can be administered in the amount of 500 mg. Ertugliflozin or a pharmaceutically acceptable salt or a co-crystal thereof can be administered in the amount of 5 mg while metformin, or a pharmaceutically acceptable salt thereof can be administered in the amount of 850 mg. Ertugliflozin or a pharmaceutically acceptable salt or a co-crystal thereof can be administered in the amount of 5 mg while metformin, or a pharmaceutically acceptable salt thereof can be administered in the amount of 1000 mg. Ertugliflozin or a pharmaceuticaly acceptable salt or a co-crystal thereof can be administered in the amount of 5 mg while metformin, or a pharmaceutically acceptable salt thereof can be administered in the amount of 1700 mg. Ertugliflozin or a pharmaceutically acceptable salt or a co-crystal thereof can be administered in the amount of 5 mg while metformin, or a pharmaceutically acceptable salt thereof can be administered in the amount of 2000 mg.

Ertugliflozin or a pharmaceutically acceptable salt or a co-crystal thereof can be administered in the amount of 7.5 mg while metformin, or a pharmaceutically acceptable salt thereof can be administered in the amount of 500 mg. Ertugliflozin or a pharmaceutically acceptable salt or a co-crystal thereof can be administered in the amount of 7.5 mg while metformin, or a pharmaceutically acceptable salt thereof can be administered in the amount of 850 mg. Ertugliflozin or a pharmaceutically acceptable salt or a co-crystal thereof can be administered in the amount of 7.5 mg while metformin, or a pharmaceutically acceptable salt thereof can be administered in the amount of 1000 mg. Ertugliflozin or a pharmaceutically acceptable salt or a co-crystal thereof can be administered in the amount of 7.5 mg while metformin, or a pharmaceutically acceptable salt thereof can be administered in the amount of 1700 mg. Ertugliflozin or a pharmaceutically acceptable salt or a co-crystal thereof can be administered in the amount of 7.5 mg while metformin, or a pharmaceutically acceptable salt thereof can be administered in the amount of 2000 mg.

Ertugliflozin or a pharmaceutically acceptable salt or a co-crystal thereof can be administered in the amount of 15 mg while metformin, or a pharmaceutically acceptable salt thereof can be administered in the amount of 500 mg. Ertugliflozin or a pharmaceutically acceptable salt or a co-crystal thereof can be administered in the amount of 15 mg while metformin, or a pharmaceutically acceptable salt thereof can be administered in the amount of 850 mg. Ertugliflozin or a pharmaceutically acceptable salt or a co-crystal thereof can be administered in the amount of 15 mg while metformin, or a pharmaceutically acceptable salt thereof can be administered in the amount of 1000 mg. Ertugliflozin or a pharmaceutically acceptable salt or a co-crystal thereof can be administered in the amount of 15 mg while metformin, or a pharmaceutically acceptable salt thereof can be administered in the amount of 1700 mg. Ertugliflozin or a pharmaceutically acceptable salt or a co-crystal thereof can be administered in the amount of 15 mg while metformin, or a pharmaceutically acceptable salt thereof can be administered in the amount of 2000 mg.

Such combinations (ertugliflozin and metformin) can be administered simultaneously or sequentially. Such combinations can be in a single pharmaceutical compositions or each pharmaceutical agent can be in a separate pharmaceutical composition. Such combinations can be can be administered once, twice or three times daily.

In certain embodiments of the methods described herein, ertugliflozin or a pharmaceutically acceptable salt or a co-crystal thereof is administered in combination with sitagliptin and metformin, or a pharmaceutically acceptable salt thereof, in any combination of the dosages for each pharmaceutical agent discussed above. Such triple combinations (ertugliflozin and sitagilptin and metformin) can be administered simultaneously or sequentially. Such triple combinations can be in a single pharmaceutical compositions or each pharmaceutical agent can be in a separate pharmaceutical composition. Such combinations can be can be administered once, twice or three times daily.

In certain embodiments, the pharmaceutical composition comprises from 0.1 to 500 mg of ertugliflozin or a pharmaceutically acceptable salt or a co-crystal thereof, or more specifically from 1 to 200 mg, from 2 to 100 mg, or from 2 to 20 mg of ertugliflozin or a pharmaceutically acceptable salt or a co-crystal thereof in combination with 1 mg to 10 mg of a sulfonylurea (SU) or a pharmaceutically acceptable salt thereof, or more specifically from 1 to 8 mg, from 1 to 6 mg, or from 1 to 2 mg of a sulfonylurea (SU) or a pharmaceutically acceptable salt thereof. In certain embodiments, the methods described herein include administering 5 mg or 15 mg of ertugliflozin or a pharmaceutically acceptable salt or a co-crystal thereof in combination with 1 mg, 2 mg or 8 mg of a sulfonylurea (SU) or a pharmaceutically acceptable salt thereof. In other embodiments, the methods described herein include administering 2.5 mg or 7.5 mg of ertugliflozin or a pharmaceutically acceptable salt or a co-crystal thereof in combination with 1 mg, 2 mg or 8 mg of a sulfonylurea (SU) or a pharmaceutically acceptable salt thereof.

Embodiments of the present invention are illustrated by the following Example. It is to be understood, however, that the embodiments of the invention are not limited to the specific details of the Example, as other variations thereof will be known, or apparent in light of the instant disclosure, to one of ordinary skill in the art.

EXAMPLE

Randomized, Double-Blind, Placebo-Controlled, Parallel Group Study to Assess Cardiovascular Outcomes Following Treatment With Ertugliflozin in Subjects With Type 2 Diabetes Mellitus and Established Vascular Disease
Summary A double-blind, randomized, Phase III study of cardiovascular outcomes following treatment with 5 mg or 15 mg of ertugliflozin orally (supplied as film-coated tablets for oral administration, containing 6.48 or 19.43 mg of ertugliflozin L-pyroglutamic acid, which is equivalent to 5 and 15 mg of the active ingredient ertugliflozin), once daily, against placebo, in participants with type 2 diabetes mellitus (T2DM) and established vascular disease. This trial includes a pre-defined glycemic sub-study in participants receiving background insulin with or without metformin, or a pharmaceutically acceptable salt thereof and another pre-defined glycemic sub-study in participants receiving background sulfonylurea (SU) monotherapy.

Current Primary Outcome Measures

Time to First Occurrence of Any Component of the Composite Endpoint of a Major Adverse Cardiovascular Event (MACE), Cardiovascular Death, Non-fatal Myocardial Infarction, or Non-fatal Stroke.

Current Secondary Outcome

Time to First Occurrence of cardiovascular death or hospitalization for heart failure; cardiovascular death; MACE plus; fatal or non-fatal myocardial infarction; fatal or non-fatal stroke; hospitalization for heart failure; individual components of MACE (cardiovascular death, non-fatal myocardial infarction, non-fatal stroke).

All-cause mortality.

All MACE events (i.e., not censored at the time of the first event).

All cardiovascular death or hospitalizations for heart failure (i.e., not censored at the time of the first event).

Time to first occurrence of the composite of renal death, renal dialysis/transplant, or 2× increase in baseline serum creatinine.

When Added to Usual Background Therapy in Subjects with T2DM and Established Vascular Disease:

Change from Baseline in HbA1c at Week 18, Week 52 and annually thereafter.

Proportion of subjects with HbA1c less than 7% (53 mmol/mol) and less than 6.5% (48 mmol/mol) at 12, 24 and 36 months and annually thereafter.

Time to the first occurrence of a subject receiving glycemic rescue therapy during the first 18 weeks of the study.

Time to initiation of insulin for subjects not on insulin at randomization.

Change in insulin dose from Baseline at Week 18, Week 52 and annually thereafter.

Change from Baseline in systolic and diastolic blood pressure at Week 18, Week 52 and annually thereafter.

Change from Baseline in body weight at Week 18, Week 52 and annually thereafter. Change from Baseline in eGFR and serum creatinine at Week 18, Week 52 and annually thereafter.

Change from Baseline in albuminuria as measured by the urinary albumin to creatinine ratio at Week 18, Week 52 and annually thereafter stratified by albuminuria category at baseline (normoalbuminuria, microalbuminuria and macroalbuminuria).

Progression of nephropathy as measured by the progression of normoalbuminuria to microalbuminuria and/or macroalbuminuria as well as measurement of regression of albuminuria (e.g., macroalbuminuria microalbuminuria).

Sub-Studies

A glycemic sub-study in subjects receiving background insulin with or without metformin, another sub-study in subjects receiving background sulfonylurea (SU) monotherapy and a sub-study in subjects receiving background metformin with SU.

Insulin with or without Metformin Add-on Glycemic Sub-Study Endpoints

Primary Endpoint

Change in HbA1c from Baseline to Week 18.

Secondary Endpoints

Change in FPG from Baseline to Week 18.

Change in body weight from Baseline to Week 18.

Proportion of subjects with an HbA1c of <7% (53 mmol/mol) at Week 18.

Change in systolic and diastolic blood pressure from Baseline to Week 18.

Change in insulin dose from Baseline to Week 18.

SU Monotherapy Add-on Glycemic Sub-Study Endpoints

Primary Endpoint

Change in HbA1c from Baseline to Week 18.

Secondary Endpoints

Change in FPG from Baseline to Week 18.

Change in body weight from Baseline to Week 18.

Proportion of subjects with an HbA1c of <7% (53 mmol/mol) at Week 18.

Change in systolic and diastolic blood pressure from Baseline to Week 18.

Metformin with SU Add-on Glycemic Sub-Study Endpoints

Primary Endpoint

Change in HbA1c from Baseline to Week 18.

Secondary Endpoints

Change in FPG from Baseline to Week 18.

Change in body weight from Baseline to Week 18.

Proportion of subjects with an HbA1c of <7% (53 mmol/mol) at Week 18.

Change in systolic and diastolic blood pressure from Baseline to Week 18.

Eligibility Criteria Inclusion Criteria:

Diagnosis of T2DM in accordance with American Diabetes Association (ADA) guidelines Hemoglobin A1c (HbA1c) at the start of study participation of 7.0-10.5% (53-91 mmol/mol)

On stable allowable anti-hyperglycemic agents (AHA) or on no background AHA for at least 8 weeks prior to the study participation Body Mass Index (BMI) greater than or equal to 18.0 kg/m$^2$ Evidence or a history of atherosclerosis involving the coronary, cerebral or peripheral vascular systems Male, female not of reproductive potential, or female of reproductive potential who agrees to be abstinent from heterosexual activity or agrees to use or have their partner use 2 acceptable methods of contraception Additional Inclusion Criteria Specific to the Insulin with and without Metformin, or a pharmaceutically acceptable salt thereof Add-on Glycemic Sub-Study Insulin >=20 units/day with or without metformin, or a pharmaceutically acceptable salt thereof >=1,500 mg/day stable doses for at least 8 weeks prior to study participation Additional Inclusion Criteria Specific to the sulfonylurea (SU) Monotherapy Add-on Glycemic Sub-Study Monotherapy with an acceptable dose of a SU. The dose of the SU monotherapy must have been stable for at least 8 weeks prior to study participation.

Exclusion Criteria:

Previous randomization into a trial of ertugliflozin

Experiencing a cardiovascular event (myocardial infarction or stroke) or undergoing coronary angioplasty or peripheral intervention procedure between the Screening Visit and randomization Undergoing any cardiovascular surgery (valvular surgery) within 3 months of study participation Planned revascularization or peripheral intervention procedure or other cardiovascular surgery New York Heart Association (NYHA) Class III or IV heart failure at study participation History of type 1 diabetes mellitus or a history of ketoacidosis Additional Exclusion Criteria Specific to the Insulin+1-Metformin, or a pharmaceutically acceptable salt thereof Add-on Glycemic Sub-Study Use of prandial insulin alone without basal insulin Pharmaceutical Formulation As a specific embodiment of an oral pharmaceutical composition, a 15 mg potency tablet is composed of 15 mg of ertugliflozin, 30 mg microcrystalline cellulose, 30 mg of dibasic calcium phosphate, 2 mg of croscarmellose sodium, 2 mg of sodium stearyl fumarate and 1 mg of magnesium stearate. The active, microcrystalline cellulose, dibasic calcium phosphate, sodium stearyl fumarate, and croscarmellose are blended first. The mixture is then lubricated by magnesium stearate and pressed into tablets. Tablets are coated with Opadry and wax.

What is claimed is:

1. A method of reducing the risk of hospitalization for heart failure in an adult with type 2 diabetes mellitus and established cardiovascular disease comprising administering to the adult of ertugliflozin or a pharmaceutically acceptable salt or a co-crystal thereof, wherein the ertugliflozin or a pharmaceutically acceptable salt or a co-crystal thereof administered is in a pharmaceutical composition comprising 0.5-15% by weight of ertugliflozin, 10-50% by weight of microcrystalline cellulose, 10-50% by weight of dibasic calcium phosphate anhydrous, 0.5-5% croscamellose sodium, 0.5-5% by weight sodium stearyl fumarate, 0.5-2% by weight magnesium stearate, 1-6% by weight Opadry 20A, and 0.001-0.005% by weight carnuba wax.

2. The method of reducing the risk of hospitalization for heart failure in an adult with type 2 diabetes mellitus and established cardiovascular disease of claim 1, wherein, the pharmaceutical composition comprises 5 mg of ertugliflozin or a pharmaceutically acceptable salt or a co-crystal thereof.

3. The method of reducing the risk of hospitalization for heart failure in an adult with type 2 diabetes mellitus and established cardiovascular disease of claim 1, wherein, the pharmaceutical composition comprises 15 mg of ertugliflozin or a pharmaceutically acceptable salt or a co-crystal thereof.

4. The method of reducing the risk of hospitalization for heart failure in an adult with type 2 diabetes mellitus and established cardiovascular disease of claim 1, wherein, the pharmaceutical composition is administered once daily.

* * * * *